(12) United States Patent
Achkire et al.

(10) Patent No.: US 12,220,270 B2
(45) Date of Patent: Feb. 11, 2025

(54) IMAGING SYSTEMS AND METHODS FOR IMAGE-GUIDED RADIOSURGERY

(71) Applicant: Zap Surgical Systems, Inc., San Carlos, CA (US)

(72) Inventors: Younes Achkire, San Francisco, CA (US); Raymond Wilbur, San Jose, CA (US); John Adler, Stanford, CA (US); Manoocher Birang, Los Gatos, CA (US); Radhika Mohan Bodduluri, Palo Alto, CA (US); Hui Zhang, San Jose, CA (US); Tom McDermott, San Carlos, CA (US); Chris Lee, San Jose, CA (US); Kaustubh Sonawale, Sunnyvale, CA (US); Cesare Jenkins, Stanford, CA (US)

(73) Assignee: Zap Surgical Systems, Inc., San Carlos, CA (US)

( * ) Notice: Subject to any disclaimer, the term of this patent is extended or adjusted under 35 U.S.C. 154(b) by 685 days.

(21) Appl. No.: 17/398,798

(22) Filed: Aug. 10, 2021

(65) Prior Publication Data

US 2021/0369217 A1     Dec. 2, 2021

Related U.S. Application Data

(63) Continuation of application No. 16/681,305, filed on Nov. 12, 2019, now Pat. No. 11,844,637, which is a
(Continued)

(51) Int. Cl.
*A61B 6/00*     (2024.01)
*A61B 6/02*     (2006.01)
(Continued)

(52) U.S. Cl.
CPC .............. *A61B 6/107* (2013.01); *A61B 6/022* (2013.01); *A61B 6/0407* (2013.01);
(Continued)

(58) Field of Classification Search
CPC ..... A61B 6/022; A61B 6/0407; A61B 6/0421; A61B 6/0487; A61B 6/107; A61B 6/12;
(Continued)

(56) References Cited

U.S. PATENT DOCUMENTS 2,595,260 A     5/1952 Hollstein
2,781,454 A     2/1957 Green et al.
(Continued)

FOREIGN PATENT DOCUMENTS

CN     2533895     2/2003
CN     1481756     3/2004
(Continued)

OTHER PUBLICATIONS

Bodduluri et al., "X-ray guided robotic radiosurgery for solid tumors", Industrial Robot: An International Journal, vol. 29, No. 3, 2002, pp. 221-227.
(Continued)

*Primary Examiner* — Dani Fox
(74) *Attorney, Agent, or Firm* — Kilpatrick Townsend & Stockton LLP

(57) ABSTRACT

A self-shielded and computer controlled system for performing non-invasive stereotactic radiosurgery and precision radiotherapy using a linear accelerator mounted within a two degree-of-freedom radiation shield coupled to a three-degree of freedom patient table is provided. The radiation shield can include an axial shield rotatable about an axial axis and an oblique shield independently rotatable about an oblique axis, thereby providing improved range of trajectories of the therapeutic and diagnostic radiation beams. Such
(Continued)

shields can be balanced about their respective axes of rotation and about a common support structure to facilitate ease of movement. Such systems can further include an imaging system to accurately deliver radiation to the treatment target and automatically make corrections needed to maintain the anatomical target at the system isocenter. Various subsystems to automate controlled and coordinated movement of the movable shield components and operation of the treatment related subsystems to optimize performance and ensure safety are also provided.

40 Claims, 15 Drawing Sheets

Related U.S. Application Data continuation of application No. 16/123,834, filed on Sep. 6, 2018, now Pat. No. 10,499,861.

(60) Provisional application No. 62/554,876, filed on Sep. 6, 2017.

(51) Int. Cl.
*A61B 6/04* (2006.01)
*A61B 6/10* (2006.01)
*A61B 6/12* (2006.01)
*A61B 6/42* (2024.01)
*A61N 5/10* (2006.01)

(52) U.S. Cl.
CPC .......... *A61B 6/0421* (2013.01); *A61B 6/0487* (2020.08); *A61B 6/12* (2013.01); *A61B 6/4241* (2013.01); *A61B 6/4258* (2013.01); *A61B 6/5235* (2013.01); *A61B 6/547* (2013.01); *A61N 5/1042* (2013.01); *A61N 5/1082* (2013.01); *A61N 2005/1054* (2013.01); *A61N 2005/1059* (2013.01); *A61N 2005/1074* (2013.01); *A61N 2005/1094* (2013.01)

(58) Field of Classification Search
CPC ... A61B 6/4241; A61B 6/4258; A61B 6/5235; A61B 6/547; A61N 2005/1054; A61N 2005/1059; A61N 2005/1061; A61N 2005/1074; A61N 2005/1094; A61N 5/1042; A61N 5/1085
See application file for complete search history.

(56) References Cited

U.S. PATENT DOCUMENTS

| | | |
|---|---|---|
| 2,818,510 A | 12/1957 | Hansheinrich |
| 2,890,349 A | 6/1959 | Laszlo |
| 3,082,322 A | 3/1963 | Koerner et al. |
| 3,281,598 A | 10/1966 | Irene |
| 3,349,242 A | 10/1967 | Braestrup |
| 3,466,439 A | 9/1969 | Setala |
| 3,488,495 A | 1/1970 | Schneeman |
| 3,588,499 A | 6/1971 | Pegrum |
| 3,617,749 A | 11/1971 | Massiot |
| 3,670,163 A | 6/1972 | Lajus |
| 3,803,418 A | 4/1974 | Holstrom |
| 3,833,813 A | 9/1974 | James |
| 3,852,598 A | 12/1974 | Larsson |
| 3,868,506 A | 2/1975 | Ogiso |
| 3,892,967 A | 7/1975 | Howarth et al. |
| 4,139,775 A | 2/1979 | Williams |
| 4,177,382 A | 12/1979 | Hounsfield |
| 4,209,706 A | 6/1980 | Nunan |
| 4,266,135 A | 5/1981 | Kuwik et al. |
| 4,288,700 A | 9/1981 | Grass et al. |
| 4,338,521 A | 7/1982 | Shaw et al. |
| 4,339,825 A | 7/1982 | Barrett et al. |
| 4,358,856 A | 11/1982 | Stivender et al. |
| 4,363,128 A | 12/1982 | Grady et al. |
| 4,481,656 A | 11/1984 | Janssen et al. |
| 4,541,108 A | 9/1985 | Grady et al. |
| 4,560,882 A | 12/1985 | Barbaric et al. |
| 4,649,560 A | 3/1987 | Grady et al. |
| 4,653,083 A | 3/1987 | Rossi |
| 4,741,015 A | 4/1988 | Charrier |
| 4,741,105 A | 5/1988 | Wong |
| 4,756,016 A | 7/1988 | Grady et al. |
| 4,827,491 A | 5/1989 | Barish |
| 4,866,751 A | 9/1989 | Louiday |
| 4,922,512 A | 5/1990 | Lajus et al. |
| 4,977,585 A | 12/1990 | Boyd |
| 4,987,585 A | 1/1991 | Kidd et al. |
| 4,998,268 A | 3/1991 | Winter |
| 5,038,371 A | 8/1991 | Janssen et al. |
| 5,040,203 A | 8/1991 | Janssen et al. |
| 5,048,069 A | 9/1991 | Siczek |
| 5,048,071 A | 9/1991 | Van |
| 5,052,036 A | 9/1991 | Grady |
| 5,054,041 A | 10/1991 | Hampel |
| 5,073,917 A | 12/1991 | Van et al. |
| 5,086,447 A | 2/1992 | Siczek et al. |
| 5,095,501 A | 3/1992 | Kobayashi |
| 5,155,757 A | 10/1992 | Sakaniwa et al. |
| 5,159,622 A | 10/1992 | Sakaniwa et al. |
| 5,207,223 A | 5/1993 | Adler et al. |
| 5,379,333 A | 1/1995 | Toth |
| 5,420,427 A | 5/1995 | Morgan et al. |
| 5,537,452 A | 7/1996 | Shepherd et al. |
| 5,577,094 A | 11/1996 | Fudamoto |
| 5,634,929 A | 6/1997 | Misko et al. |
| 5,699,446 A | 12/1997 | Rougee et al. |
| 5,751,781 A | 5/1998 | Brown et al. |
| 5,757,886 A | 5/1998 | Song |
| 5,835,557 A | 11/1998 | Malmstroem |
| 5,945,684 A | 8/1999 | Lam et al. |
| 6,104,779 A | 8/2000 | Shepherd et al. |
| 6,155,713 A | 12/2000 | Watanabe |
| 6,198,957 B1 | 3/2001 | Green |
| 6,217,214 B1 | 4/2001 | Cabral et al. |
| 6,309,102 B1 | 10/2001 | Stenfors |
| 6,325,538 B1 | 12/2001 | Heesch |
| 6,512,813 B1 | 1/2003 | Krispel et al. |
| 6,614,871 B1 | 9/2003 | Kobiki et al. |
| 6,789,941 B1 | 9/2004 | Grady |
| 6,856,670 B2 | 2/2005 | Hoheisel |
| 6,888,919 B2 | 5/2005 | Graf |
| 6,969,194 B1 | 11/2005 | Naefstadius |
| 7,188,999 B2 | 3/2007 | Mihara et al. |
| 7,193,227 B2 | 3/2007 | Hiramoto et al. |
| 7,239,684 B2 | 7/2007 | Hara et al. |
| 7,295,648 B2 | 11/2007 | Brown |
| 7,302,038 B2 | 11/2007 | Mackie et al. |
| 7,473,913 B2 | 1/2009 | Hermann et al. |
| 7,502,443 B1 | 3/2009 | Haynes et al. |
| 7,526,066 B2 | 4/2009 | Koshnitsky et al. |
| 7,649,981 B2 | 1/2010 | Seppi et al. |
| 8,139,714 B1 | 3/2012 | Sahadevan |
| 8,406,844 B2 | 3/2013 | Ruchala et al. |
| 8,602,647 B2 | 12/2013 | Navarro |
| 8,913,716 B2 | 12/2014 | Sobering et al. |
| 9,014,341 B2 | 4/2015 | Zhang et al. |
| 9,208,918 B2 | 12/2015 | Tybinkowski et al. |
| 9,308,395 B2 | 4/2016 | Adler, Jr. et al. |
| 9,314,160 B2 | 4/2016 | Adler, Jr. et al. |
| 9,604,077 B2 | 3/2017 | Xing et al. |
| 9,757,593 B2 | 9/2017 | Adler et al. |
| 11,058,892 B2 | 7/2021 | Wilbur et al. |
| 11,826,582 B2 | 11/2023 | Wilbur et al. |
| 11,844,637 B2 | 12/2023 | Jenkins et al. |
| 2004/0066889 A1 | 4/2004 | Swift |
| 2004/0136495 A1 | 7/2004 | Carlsson et al. |
| 2004/0149924 A1 | 8/2004 | Russell |
| 2004/0170254 A1 | 9/2004 | Gregerson et al. |
| 2004/0251419 A1 | 12/2004 | Nelson et al. |

(56) References Cited

U.S. PATENT DOCUMENTS

| | | |
|---|---|---|
| 2005/0049477 A1 | 3/2005 | Fu et al. |
| 2005/0141671 A1 | 6/2005 | Pastyr et al. |
| 2005/0197564 A1 | 9/2005 | Dempsey |
| 2005/0236588 A1 | 10/2005 | Ein-Gal |
| 2006/0245548 A1 | 11/2006 | Callerame et al. |
| 2007/0014391 A1 | 1/2007 | Mostafavi et al. |
| 2007/0189591 A1 | 8/2007 | Lu et al. |
| 2008/0002809 A1 | 1/2008 | Bodduluri |
| 2008/0144908 A1 | 6/2008 | West et al. |
| 2008/0212738 A1 | 9/2008 | Gertner et al. |
| 2009/0086909 A1 | 4/2009 | Hui et al. |
| 2009/0103686 A1 | 4/2009 | Rothschild |
| 2009/0110146 A1 | 4/2009 | Sliski et al. |
| 2009/0163799 A1 | 6/2009 | Erbel et al. |
| 2009/0180678 A1 | 7/2009 | Kuduvalli et al. |
| 2010/0002829 A1 | 1/2010 | Dafni |
| 2010/0094119 A1 | 4/2010 | Yu et al. |
| 2010/0183196 A1 | 7/2010 | Fu et al. |
| 2010/0237259 A1 | 9/2010 | Wang |
| 2010/0239066 A1 | 9/2010 | Conolly et al. |
| 2010/0268074 A1 | 10/2010 | Van Loef et al. |
| 2011/0210261 A1 | 9/2011 | Maurer, Jr. |
| 2013/0114872 A1 | 5/2013 | Chen et al. |
| 2013/0136239 A1 | 5/2013 | Laws et al. |
| 2013/0188856 A1* | 7/2013 | Adler, Jr. ............... A61B 6/463 |
| | | 382/132 |
| 2013/0261430 A1 | 10/2013 | Uhlemann |
| 2014/0140471 A1 | 5/2014 | Tybinkowski et al. |
| 2015/0265852 A1 | 9/2015 | Meir et al. |
| 2016/0095558 A1 | 4/2016 | Choy et al. |
| 2016/0220848 A1 | 8/2016 | Adler, Jr. et al. |
| 2016/0317839 A1 | 11/2016 | Prionas et al. |
| 2017/0281972 A1 | 10/2017 | Zhang et al. |
| 2018/0318607 A1 | 11/2018 | Wilbur et al. |
| 2019/0001146 A1 | 1/2019 | Liu |
| 2020/0038685 A1 | 2/2020 | Kundapur et al. |

FOREIGN PATENT DOCUMENTS

| | | |
|---|---|---|
| CN | 1666301 | 9/2005 |
| CN | 2772541 | 4/2006 |
| CN | 1785454 | 6/2006 |
| CN | 1919372 | 2/2007 |
| CN | 101069644 | 11/2007 |
| CN | 101496727 | 8/2009 |
| CN | 102441238 | 5/2012 |
| CN | 103185914 | 7/2013 |
| CN | 106237545 | 12/2016 |
| CN | 106267587 | 1/2017 |
| CN | 106456991 | 2/2017 |
| CN | 106512221 | 3/2017 |
| CN | 106908827 | 6/2017 |
| CN | 107101712 | 8/2017 |
| CN | 108401421 | 8/2018 |
| DE | 3321057 | 12/1984 |
| DE | 19604789 A1 | 8/1997 |
| DE | 19728788 | 1/1999 |
| EP | 1075855 | 2/2001 |
| FR | 1587608 | 3/1970 |
| GB | 1129653 | 10/1968 |
| JP | 6082300 | 6/1985 |
| JP | 01502401 | 8/1989 |
| JP | 04221532 | 8/1992 |
| JP | 2885304 | 12/1993 |
| JP | 0767975 | 3/1995 |
| JP | 07163669 | 6/1995 |
| JP | H07255867 | 10/1995 |
| JP | H07265445 | 10/1995 |
| JP | 2000271109 | 10/2000 |
| JP | 2001137372 | 5/2001 |
| JP | 2003024459 | 1/2003 |
| JP | 2003205042 | 7/2003 |
| JP | 2003210596 | 7/2003 |
| JP | 2004097646 | 4/2004 |
| JP | 2007148276 | 6/2007 |
| JP | 2010519965 | 6/2010 |
| JP | 2012183283 | 9/2012 |
| NL | 7215879 | 5/1973 |
| WO | 0074779 | 12/2000 |
| WO | 0112262 | 2/2001 |
| WO | 03018131 | 3/2003 |
| WO | 2003077763 | 9/2003 |
| WO | 2008024463 | 2/2008 |
| WO | 2012040964 | 4/2012 |
| WO | 2013180883 | 12/2013 |
| WO | 2015096572 | 7/2015 |
| WO | 2017020244 | 2/2017 |
| WO | 2017041750 | 3/2017 |
| WO | 2017083026 | 5/2017 |
| WO | 2017100611 | 6/2017 |
| WO | 2018203918 | 11/2018 |

OTHER PUBLICATIONS

Dong et al., "An Image Correlation Procedure for Digitally Reconstructed Radiographs and Electronic Portal Images", Int. J. Radiation Oncology Biol. Phys., vol. 33, No. 5, 1995, pp. 1053-1060.

Hissoiny et al., "GPUMCD: a new GPU-Oriented Monte Carlo dose calculation platform", physics.med-ph, Jan. 2011, 28 pp.

Jung et al., "Flexible Gd2O2S:Tb scintillators pixelated with polyethylene microstructures for digital x-ray image sensors", J. Micromech. Microeng. 19, 2009, 10pp.

Lo et al., "Hardware acceleration of a Monte Carlo simulation for photodynamic treatment planning", Journal of Biomedical Optics, vol. 14(1), Jan./Feb. 2009, pp. 014019-1 thru 014019-11.

Mackie et al., "Tomotherapy: a new concept for the delivery of dynamic conformal radiotherapy.", Medical Physics 20, 1709 (1993); doi: 10.1118/1.596958, Jun. 4, 1998, 1709-1719.

Osher et al., "Fast Linearized Bregman Iteration for Compressive Sensing and Sparse Denoising", 2008, pp. 1-19.

PCT/US2017/038256 International Search Report and Written Opinion mailed Sep. 11, 2017, 12 pages.

Ruchala et al., "Megavoltage CT image reconstruction during tomotherapy treatments", Phys. Med. Biol. vol. 45, 2000, pp. 3545-3562.

Schonberg, "The History of the Portable Linear Accelerator", American Association for Physicists in Medicine, downloaded from the internet: https://www.aapm.org/meetings/2001AM/pdf/7221-68900.pdf, 2001, pp. 1-14.

Weidlich et al., "Characterization of a Novel Revolving Radiation Collimator", Cureus, vol. 10, No. 2, Feb. 2, 2018, pp. 1-9.

Zaman et al., "Scintillating Balloon-Enabled Fiber-Optic System for Radionuclide Imaging of Atherosclerotic Plaques", J Nucl Med 56(5), 2015, 771-777.

* cited by examiner

IMAGING SYSTEMS AND METHODS FOR IMAGE-GUIDED RADIOSURGERY

CROSS-REFERENCE TO RELATED APPLICATIONS

The present application is a Continuation of U.S. patent application Ser. No. 16/681,305 filed Nov. 12, 2019, which is a Continuation of U.S. patent application Ser. No. 16/123,834 filed Sep. 6, 2018 (now U.S. Pat. No. 10,499,861); which claims the benefit of U.S. Provisional Appln. No. 62/554,876 filed Sep. 6, 2017; and PCT Appln. No. PCT/US2017/054880 filed Oct. 3, 2017; the full disclosures which are incorporated herein by reference in their entirety for all purposes.

This application is generally related to PCT Application No. PCT/US2017/038256 filed Jun. 20, 2017 entitled "Revolving Radiation Collimator;" U.S. Pat. No. 9,308,395 entitled "Radiation Systems with Minimal or No Shielding Requirements on Building;" U.S. Pat. No. 9,314,160 entitled "System and Method for Real-Time Target Validation for Image-Guided Radiation Therapy;" and U.S. Pat. No. 9,604,077 entitled "Visualizing Radiation Therapy Beam in Real-Time in the Context of Patient's Anatomy;" each of which is incorporated herein by reference in its entirety for all purposes.

BACKGROUND OF THE INVENTION

The present invention relates generally to the field of stereotactic radiosurgery. In particular, the invention relates to self-shielded radiation treatment systems and methods of treatment.

The high-cost of building radiation-shielded rooms for radiosurgery equipment has created a need for systems that can be offered at a lower cost. Creating a radiosurgical system that is self-shielded accomplishes this objective, but there are challenges associated with such systems, including complex coordinated function of numerous subsystems to ensure safe and effective treatment delivery.

While various self-shielded radiosurgical systems have been proposed, there are considerable challenges encountered in executing such systems, which include the high cost and weight of the shielded components, the difficulties in positioning shielded components due to their considerable weight, and the considerable cost and size of the associated supports and driving motors that further add to the size and weight of the overall system. These challenges limit the feasibility of such designs and further limit the range of available trajectories of treatment. Therefore, there is a need for self-shielded systems having reduced weight and size, and further need for such systems with improved dexterity and range of movement for a therapeutic radiation beam and diagnostic imaging. It would be desirable for such systems to be constructed more simply and cost effectively and to have a compact size and reduced footprint so as to fit in a standard sized room without requiring a conventional vault or radiation-shielded room, to allow such treatment systems to be more widely available for treatment.

BRIEF SUMMARY OF THE INVENTION

The treatment systems described herein are self-shielded and computer controlled systems for planning and performing non-invasive stereotactic radiosurgery and precision radiotherapy.

In some aspects, the present invention provides substantial advantages over conventional self-shielded designs by use of a unique shield design and placement that minimizes the amount and weight of shielding that prevents potential radiation escape, while fulfilling the objectives of maintaining anatomical target at isocenter of system, providing maximal range of MV and kV beam trajectories via independent axial and oblique shields, and providing mechanical advantages of symmetrically balancing heavy radiation shield components about a relatively small footprint base ring for a common support. In various embodiments, providing variable thickness of shields minimizes weight, and balancing the shields in space enables more precise movement of the shield and therapeutic radiation beam. In one aspect, the invention provides a self-shielded design with movable shield components providing the benefits described herein and further providing total encapsulation of the patient so as to provide total shielding. In some embodiments, such a system includes axial and oblique shields, as well as a rotary shell and door that allows for complete encapsulation of the patient and total shielding.

Such systems can include a therapeutic radiation beam emitter, such as a linear accelerator (LINAC), mounted on a two degree-of-freedom rotatable shield assembly, and an imaging system to accurately deliver radiation to the treatment target (e.g. a brain tumor of the patient). In some embodiments, the system includes three independent degrees of freedom associated with a patient table, added to the two axis of freedom for the LINAC to provide a total of five degrees of freedom for positioning a target accurately in the iso-center.

In some embodiments, the system uses radiographic information on a patient anatomy (e.g. skull position) to track the patient movement and corrects for detected patient movement by adjusting the surgical table precisely to locate the target at an isocenter of the rotatable shield assembly. The treatment system includes various hardware and software systems integrally related in the function of the overall system. Subsystems include: mechanical subsystem, patient table subsystem, integrated control subsystem, LINAC subsystem, treatment planning subsystem, treatment delivery subsystem, imaging and monitoring subsystems, control subsystem, safety subsystem. Each of these subsystems can include corresponding hardware and software components within an integrated robotic system. It is appreciated that the overall system is not required to include all the subsystems described herein and associated features and can include one or more of the subsystems, modifications of the described subsystems, or any combination thereof.

In a first aspect, the systems and methods described herein are configured to maintain an anatomical target at an iso-center of the system. In some embodiments, the system includes one or more cameras that can be used for monitoring of a patient and can also be used to determine and/or verify an isocenter of the system. Such cameras can be incorporated into the collimator assembly, mounted within a movable shield component or mounted to an adjacent structure above the patient table. In some embodiments, the collimator includes two such cameras directed towards the patient. In some embodiments, the system includes at least two or more, often four cameras, mounted in a fixed location above a patient table, such that the cameras do not move when the radiation shield components are rotated. In some embodiments, the system can include one or more cameras that are independently positionable.

In a second aspect, the systems and methods described herein maintain a self-shielded environment. In some embodiments, the self-shielded environment is maintained by coordinated movement of multiple shield components, at least a first and second shield component that movably interface.

In a third aspect, the systems and methods described herein provide an improved or maximal range of both MV and kV beam trajectories for treatment and imaging via independent axial and oblique shields. In such systems, the kV beam emitter can be mounted in the axial shield component, while the MV beam emitter is mounted within the oblique shield component, which is rotatable about an oblique axis transverse to the axial axis of the axial shield component.

In a fourth aspect, the systems and methods described herein provide a mechanical advantage by symmetrically balancing shields. In some embodiments, the multiple shield components are supported by a support ring having relatively small footprint as compared to the overall size of the system. In some embodiments, mechanical advantages are provided by symmetrically balancing shields about a common support with relatively small footprint base, permitting shields to be moved with greater ease and accuracy. In some embodiments, a base ring acts as the common support that facilitates precision and accuracy.

In a fifth aspect, the systems and methods described herein provide a variable thickness of oblique shield to minimize the overall weight of system. Portions of the shield components with less exposure to a megavolt (MV) therapy radiation beam and/or a kilovolt (kV) diagnostic radiation beam can have reduced thickness. Such variable thickness shielding can be formed by mounting additional sheets of shielding along the outside of shield portions with higher radiation exposure or can be fabricated by variable thickness castings.

In a sixth aspect, the systems described herein are balanced such that the weight of the LINAC shield counterbalances the weight of the beam stop. This balancing provides a mechanical advantages that allows for movement of the LINAC shield with a relatively small, lower torque motor. For instance, if the Center of Gravity (COG) of the moving parts around the axial axis was off centered (e.g. 5 mm) creating imbalance, then the maximum value of the oscillating torque induced by gravity to counter act the imbalance would be the weight of the moving shields×Off center COG distance to axis of rotation (e.g. 14000 kg×5e-3 m=700 kg·m) which is beyond what the existing motor nominal rated torque is (e.g. 300 kg·m).

DETAILED DESCRIPTION OF THE INVENTION

Figure 1:
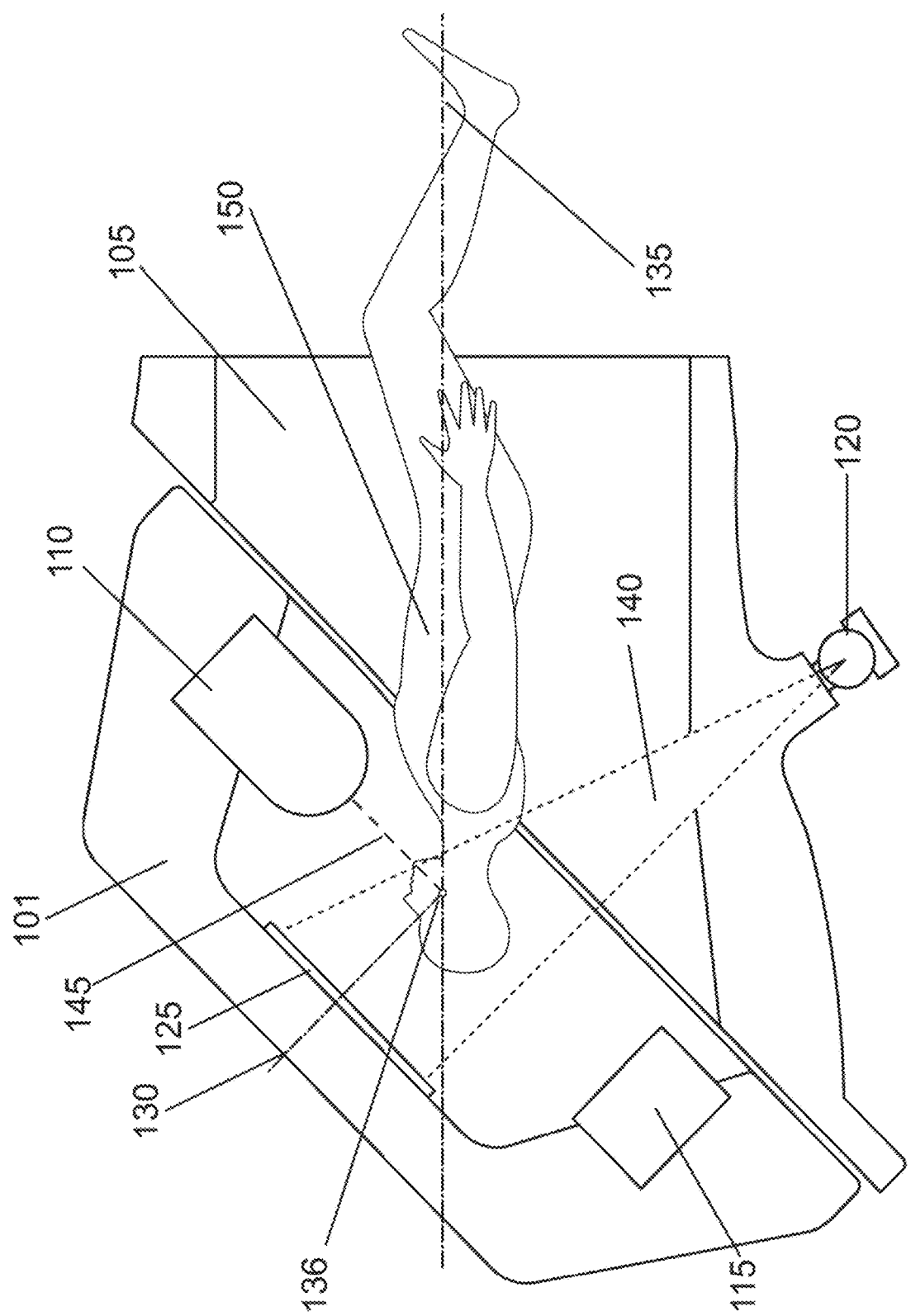
FIG. 1 illustrates an overview of a treatment system in accordance with some embodiments of the invention.

The present invention pertains to self-shielded radiation treatment system, in particular self-shielded systems having a radiation shield defined by at least two shield components that are balanced and movably interfaced so that the shield assembly rotates about a first axis and one of the shield components rotates about a second axis transverse to the first axis. Such a configuration allows for diagnostic intensity (kKV) imaging from multiple directions for tracking the patient's position by rotation of the shielding assembly and further allows for delivery of therapeutic radiation from a range of directions by independent rotation of one shield component along the second axis. Balancing of the shield components about their respective axes of rotation and about a common support and providing shield components of variable thickness substantially reduces the weight of the shielding and makes coordinated and precise controlled movement feasible. This approach also allows for system and drive assembly of more compact size, so as to fit in a standard sized room without requiring an extensive shielding vault common to conventional radiation treatment systems. In some embodiments, this configuration allows the main portion including the radiation shield to be about 3 meters or less in height and width and about 30 tons or less in weight for a 3 MV system. It is understood that the size and amount of shield depends on the radiation energy capacity of the system being used and that the concepts herein could apply to any radiation treatment system. Various aspects can be further understood by reference to the descriptions and example embodiments described herein.

I. SYSTEM OVERVIEW

In some embodiments, the radiosurgery system includes the following hardware subsystems and software: mechanical subsystem, patient table subsystem, control subsystem, linear accelerator (LINAC) subsystem, treatment planning subsystem, treatment delivery subsystem, imaging and monitoring subsystem, safety subsystem, and associated software components. It is understood that the integrated control system, safety subsystem and software components can be incorporated into a single control unit or subsystem. Alternatively, these subsystems could include multiple coordinated subsystems or units. Each of these subsystems has corresponding hardware and software components within an integrated robotic system. It is appreciated that embodiments could include some or any combination of the components, or variations thereof.

In the embodiments of the treatment systems described herein, at least two forms of radiation are emitted and detected: (1) mega-volt (MV) X-ray radiation, which is of therapeutic intensity (e.g. sufficient radiation dosage delivery to kill tumor cells) and (2) kilo-volt (kV) X-ray radiation, which is of diagnostic intensity, and is used to track the position of a target (e.g. the patient's skull or body parts) within the apparatus to ensure proper MV beam targeting and delivery. In some embodiments, the MV radiation source is affixed within one movable shield component and the kV radiation source is affixed within the other shield component, the shield components together defining a shielded treatment space around the target and being movable so as to allow imaging of the target with the kV radiation source from a multiple directions and treatment of the target from the MV radiation source from multiple directions.

A. Movable Shielding Components

In one aspect, the radiation shield includes a first shield component or axial shield that is movable about a first axial axis, typically horizontal, that is movably interfaced with a second shield component or oblique shield that is independently rotatable about a second oblique axis that is transverse to the first axis. In some embodiments, the first axial shield has a generally vertically oriented proximal opening through which the patient table and patient are inserted into the treatment space and a distal angled opening (e.g. 45 degrees) that is movably interfaced with the second shield or oblique shield such that second axis intersects the first axis at a 45 degree angle. In some embodiments, the oblique axis is generally semi-spherical in shape and includes a therapeutic radiation beam emitter and beam stop on opposite sides to allow delivery of a therapeutic radiation beam to the target from a path that encircles the target. Coordinated movement of the shields along the first axial axis and movement of the oblique shield along the second oblique axis allows for a substantially continuous range of the therapeutic beam along a majority of a surface of a treatment sphere with only a small portion of the sphere at the proximal and distal ends being inaccessible.

Typically, the first and second shields are formed of iron or iron alloy, or any suitable shield material. Additional shielding of any suitable material, same or different, can be mounted to the outside of each shield in areas exposed to higher radiation levels. In some embodiments, the treatment radiation source or treatment radiation beam emitter (e.g. LINAC) is affixed within one of the shields, while the diagnostic imaging radiation source is disposed within the other shield. The shield components can further include counterweight mounted so as to balance each shield component or assembly about their respective axes of rotation.

B. Mechanical Subsystem

In another aspect, the self-shielded radiation treatment system includes a mechanical subsystem that coordinates movement of the movable shield components to facilitate imaging and treatment from multiple directions. In some embodiments, the mechanical subsystem includes a two degree of freedom rotary electro-mechanical shield assembly that houses the LINAC and imaging subsystems. Its purpose is to move the LINAC so as to direct the high-energy treatment beam generated by the LINAC to point at the system isocenter (e.g. where the target or tumor will be located) in a precise fashion. The two degrees of freedom allows a variety of angles of approach for the treatment beam to be achieved.

In some embodiments, the system includes a rotary shell attached to the mechanical rotatable shield assembly that houses a patient table subsystem with a vertical door at the end of the rotary shell that moves up and down. These two mechanisms serve as the patient entry/exit to the system.

In various embodiments described herein, the mechanical subsystem includes:

1. Two moving radiation shields (e.g. axial shield & oblique shield) which support the radiation treatment beam generator components.
2. A central main base ring that supports the axial and oblique shields, typically through a bracket with the two rotation axis bearing.
3. A patient entry assembly that supports patient table and additional static radiation shield.
4. Rotary shell along with a vertical radiation shield that compose the entrance and exit to the treatment space.

In order to provide a head and neck treatment beam solid angle that would exceed $2\pi$ steradian, the treatment radiation beam generator components are integrated on the oblique radiation shield supported within an oblique support bracket with two degrees of freedom. In some embodiments, the system is configured to provide the largest solid angle coverage. Those degrees of freedom are transverse to each other. In the described embodiments, those degrees of freedom are pure rotations along:

1. An axial axis which is horizontal (i.e., perpendicular to gravity)
2. An oblique axis that is oriented 45 degree with respect to the axial axis. This 45 degree angle remains constant between those two axes.

In one aspect, those two axes of motion of the two movable shield components intersect at the isocenter of the treatment system in which the patient tumor is located. In some embodiments, a moving patient table subsystem can be used to ensure the target remains at the isocenter. In the described embodiments, the therapeutic radiation beam generator (i.e. LINAC) is integrated such that the beam aims at the isocenter for any position of the radiation shields. In some embodiments, the two movable shield components are supported by a common support, typically a main base ring. This can be accomplished by balancing of the two movable shield components about the support, as described further below. Typically, the base ring is of casted construction and can be anchored to the ground using structural anchoring methods. This configuration reduces the footprint of the overall treatment system. The axial rotation of the radiation shields can be accomplished using a large slew ring ball bearing. The outer ring of the slew ring bearing can be mounted to the main base ring. The axial bearing is sized to provide the required stiffness to minimize the deflection of the bearing due to the applied external forces (i.e., gravity and magnetic attraction load induced by the linear motor). The inner ring of the axial bearing is clamped between two rotating assemblies: the axial radiation shield and the oblique radiation shield-mounting bracket ("treatment bracket"). The axial shield along with the treatment bracket revolve together around the axial bearing axis driven by a linear ring motor that includes a set of linear magnet crescents mounted at the periphery of oblique shield mounting bracket, a large cage-like structure that encloses the oblique shield and associated electronic equipment, and which is visible from the posterior side of the machine. In order to provide enough torque to rotate the axial assembly, the system uses two motor coil assemblies that include a set of six coils each. Those two assemblies are located side by side at the bottom of the system main ring assembly to provide a counter moment to the moment due to the moving assembly gravity load. The axial motion position, velocity and acceleration is controlled using one ring scale along with two redundant encoder head sensors. While a particular configuration of the axial bearing and motor assemblies are described here, it is appreciated that various other configurations and any suitable motor assemblies can be used to provide rotation of the axial shield and oblique shields along the axial bearing axis in keeping with the described concepts.

In another aspect, the oblique shield is independently rotatable along a second axis transverse to the axial bearing axis. In the embodiments described herein, the oblique shield is mounted on the oblique treatment bracket through the oblique slewing ball bearing, which has a rotation axis oriented at 45 degrees with respect to the axial bearing axis. The oblique slew ring ball bearing is sized to provide a required stiffness to minimize the deflection of the bearing due to the external forces that include the gravity and the magnetic attraction load induced by the linear motor. In some embodiments, the treatment bracket is one part on which both axis bearing lodgings are machined, which avoids stackup of tolerances if using more than one bracket and ensures optimal accuracy. The radiation treatment beam generator components are integrated on the oblique radiation shield such that the treatment beam generator can be rotated entirely around the target. In order to provide enough torque to rotate the oblique shield assembly around the oblique axis, the rotating shield utilizes two identical motor coil assemblies. Typically, each motor coil assembly includes a set of six motor coils. In this embodiment, oblique shield assembly and the motor coil assemblies are mounted symmetrically in order to vanish the moment due to the coil/magnet attraction force. This attraction force induces a constant compressive axial load for the bearing, which is beneficial. In some embodiments, the oblique motion position, velocity and acceleration can be controlled using one ring scale along with two redundant encoder head sensors. It is appreciated that various other configurations can be used.

In yet another aspect, the treatment system can include a patient entry assembly to facilitate entry of the patient into the shielded treatment space defined by the axial and oblique shields. Typically, the patient entry assembly remains static with respect to the rotating axial and oblique radiation shields. In the embodiments described herein, the patient entry assembly is mounted to the main base ring and includes a radiation shield block as shown in the accompanying figures, a mount for the patient table, and a rotary shell that serves as a radiation shield rolling door for the self-shielded capsule system. The rotary shell rotates around the patient table mount by means of a geared slewing ball bearing mounted to the patient entry bracket. The geared bearing can be rotated using a pinion driven by a geared electrical motor assembly. The geared motor is equipped with a brake that is activated in the loss/absence of electrical power to the system to maintain the rotary shell in its position. A radiation-shielded vertical door assembly moves vertically to open/close the patient entry of the rotary shell. This radiation shield vertical door moves up and down using an actuator. In some embodiments, the door system is configured such that in the case of a power loss, the door can be moved down and the patient entry opened without power to allow the patient to be removed. For example, the door could be opened without power in a controlled manner by manually opening a pressure relief valve, releasing the energy induced by the large vertical gravity load.

In still another aspect, a collimator assembly can be mounted to the LINAC subsystem. An example of collimator assemblies suitable for incorporation into the treatment systems are detailed further in PCT Application No. PCT/US2017/038256. In such embodiments, the collimator assembly is spherical/cylindrical and is centered on the LINAC radiation beam axis. This mechanical axis intersects at the isocenter. Typically, the collimator assembly provides a selectable set of different collimator sizes. To achieve this later, those different collimator sizes can be designed into a revolver. To select the different collimator size, the revolver rotates via a harmonic drive (e.g., geared) electrical motor around an axis perpendicular to the LINAC radiation beam axis. This geared motor can be integrated onto the main housing, for example, as shown in the accompanying figures. A set of two redundant rotation encoder head sensors along with a scale can be mounted to the revolver to provide the position control feedback of the revolver to align each collimator size with the LINAC beam axis. In some embodiments, an additional "collimator size" sensor can be used to determines the proper position/alignment of each collimator size. The collimator assembly can be mounted onto the oblique shield, aligned with the beam axis intersecting the isocenter. Across from this collimator assembly, a radiation beam stop can be mounted. More shielding can be integrated around the LINAC to shield the backward scattering radiation from the LINAC target. The collimator and the radiation beam stop can be constructed of any suitable material, although typically, they are formed of tungsten or a tungsten alloy, which allow for a collimator and beam stop of reduced size for incorporation into the described treatment systems.

C. Patient Table Subsystem

In some embodiments, the treatment system includes a movable patient support table that is sufficiently movable along multiple axes to allow at least the portion of the patient having the target to be positioned within the treatment space defined by the movable shield components. In the embodiments described herein, the patient table includes a three-axis mechanism that serves at least two objectives—first, to provide a bed support on which the patient can lie down comfortably during treatment, and second, to accurately maintain position, in three dimensions, of a desired point in the head and neck region at the isocenter, where radiation will be delivered. To accomplish these objectives, the patient table can be defined by multiple components that allow for movement of the patient along multiple axes. In some embodiments, the patient table has at least four sub-sections—lower cart, upper cart, pitch plate and patient bed. The lower cart has the function of moving the patient between treatment and extraction positions. In order to set up the patient for treatment, patient table extends in a linear rolling fashion, from the shield assembly to the outside of the patient portal. The upper cart, pitch plate and patient bed together provide the motion needed to accurately position a point in the head and neck at the isocenter. The upper cart houses the control components for the patient table. The lower cart, upper cart and patient bed are actuated by linear motors, while the pitch plate is actuated by a rotary motor with a lead screw arrangement. A head support portion of the patient table can include facets with which to secure commercially available radiation face masks, and the patient bed can further include a restraining strap to prevent patient body from significant movement during delivery. In some embodiments, the head portion can further be configured to pitch the patient's head to further increase the available treatment range of the LINAC. It is appreciated that the treatment system can utilize a multi-axis patient table without the movable head portion as well.

In some embodiments, the patient table has at least five sub-sections—table base, lower cart, upper cart, pitch plate and patient bed. The table base provides a fixed support for the patient table. The table base acts as the interface between the patient table and the mechanical subsystem, that is, the patient table can be attached to the mechanical system using the table base. The table base can also provide additional shielding. The lower cart performs linear motion (Y1 axis) and serves the function of moving the patient between treatment and extraction positions. The lower cart can be driven by any suitable motor. In some embodiments, the lower cart is driven by a linear motor using direct drive with no transmission. Such a configuration avoids any power loss that happens in case of a mechanical transmission like a gear train. Direct drive is also more responsive. In addition, this configuration is back-drivable which can be an important safety feature. In case of power failure, the lower cart can be pulled out manually due to its back-drivability. The upper cart performs linear motion (Y2 axis), which along with the pitch plate and patient bed, provides the motion needed to accurately position a point in the head and neck region at the isocenter. The upper cart can be driven by any suitable motor, for example, a linear motor having the advantages as discussed above. The pitch plate can tilt up and down (pitch axis) and, along with the upper cart and patient bed, provide the motion needed to accurately position a point in the head and neck region at the isocenter. In some embodiments, the pitch plate is tilted up and down using a lead screw driven by a rotary motor. Such a configuration is advantageous since the lead screw is not back-drivable and hence will hold its position during an accidental power loss. The patient bed can perform an arced side to side rotation (yaw axis) motion driven by any suitable motor. In some embodiments, the yaw rotation is directly driven by a curved linear motor, which, along with the upper cart and pitch plate, provides the motion needed to accurately position a point in the head and neck region at the isocenter. Such a configuration is back-drivable as well. From a targeting perspective, the described patient table configurations serve to locate a spatial point {x,y,z} within the patient, at the isocenter (three degrees of freedom provided by the three axes).

In some embodiments, the patient table includes one primary and one redundant encoder per axis. The link between system computer and motion controller can be directly wired or Ethernet. The link between motion controller and motor drives can be directly wired or EtherCAT. Motor drives, motors, and encoders are typically located in patient table assembly.

In another aspect, the treatment planning subsystem is configured to be compatible with the patient table subsystem at the reference frame level in the world coordinate system. The treatment delivery subsystem accounts for any possible changes to the patient setup before treatment is delivered by moving the patient with the patient table so that the anatomic target area is at the physical isocenter of the system, and this function is continued throughout treatment to compensate for any patient movement detected by the imaging subsystem.

D. Integrated Control Subsystem

In yet another aspect, the system can include a motion control subsystem that collectively works to coordinate device position sensor input with the various motors on the mechanical subsystem and patient table subsystem to move the various components of the mechanical subsystem and patient table to ensure that each radiation beam is properly aimed at the target within the patient's body, and at assigned trajectories to the same at the proper times. This ensures that radiation goes only to the anatomical target. This also enables shielded patient port to be closed when necessary and open when necessary. These objectives can be achieved by interactively networking the mechanical subsystem, LINAC subsystem, treatment planning subsystem, treatment delivery subsystem, imaging and monitoring subsystem, patient table subsystem, and control and safety subsystem.

Communications between the computer, sensors and actuators can be implemented by any suitable means, for example using an EtherCAT realtime network (e.g., Beckhoff, Lenze, Sanyo-Denki, ACS) to monitor peripheral sensors and devices and control systems and actuators from a main computer system.

E. LINAC Subsystem

In still another aspect, the system includes a LINAC subsystem that produces the treatment beam. Typically, the LINAC subsystem is affixed within the second movable shield component (e.g. oblique shield component) such that movement of the shield component rotates the LINAC entirely about the target. The system can be configured to generate a charged particle treatment beam or a photon treatment beam. In some embodiments, the system uses a LINAC to produce a treatment beam with a nominal energy of 1 to 5 MeV, preferably 2 to 4 MeV, more preferably 3 MeV for a dose rate within a range of 1400 to 1600 cGy/min. In some embodiments, the systems is configured to produce a treatment beam with an energy within a range of 2-3 MV for a dose rate within a range from 1000 to 2000 cGy/min. In one aspect, the treatment beam is collimated to produce one a suitable treatment beam. In some embodiments, the LINAC subsystem is configured to produce a range of differing field sizes, for example field sizes within a range of 4 to 50 mm. In the embodiment shown, the LINAC subsystem includes eight available field sizes, such as diameters of 4 mm, 5 mm, 7.5 mm, 10 mm, 12.5 mm, 15 mm, 20 mm and 25 mm at the Source to Axis distance (SAD) of, for example 450 mm. It is appreciated that the LINAC subsystem could be configured to provide a collimated beam at various other diameters as needed for a particular therapy or target size. Each of the field sizes may be circular and symmetric, or may be square, rectangular, or any other shape desired. In some embodiments, the LINAC comes with a variety of safety interlocks which are integrated in to the control and safety subsystem.

The LINAC subsystem can include any suitable components needed to deliver a given radiation therapy to the target from multiple directions. In the embodiment described herein, the LINAC subsystem includes the LINAC, motorized secondary collimators, magnetron, solid state modulator, gun drive power supply, RF waveguide, dosimeter board, automatic frequency control (AFC) board, and LINAC control board. In some embodiments, the LINAC is configured such that the single photon beam energy is in the range of 3 MV. In some such embodiments, the depth dose=40±2% for 2.5 cm circular field size at 45 cm Source to Surface Distance (SSD) with an ionization ratio of $d_{200}/d_{100}=0.5$. In other such embodiments, the depth dose maximum ($D_{max}$) is 7+/−1 mm. In some embodiments, the dose rate is 1500+/−10% MU/min at 450 mm Source to Axis Distance (SAD); 1 MU=1 cGy at SAD=450 mm, 25 mm field size at $D_{max}$. In some embodiments, the LINAC subsystem includes a custom LINAC control board, automatic frequency control board (AFC), dosimeter and dosimeter board for incorporation into a self-shielded treatment system in accordance with aspects of the present invention.

F. Imaging & Monitoring Subsystems

In order to meet certain radiosurgical precision requirements, the treatment system can include an imaging and monitoring subsystem that provides a means of tracking the position of the tumor with respect to the system isocenter. In some embodiments, for tracking purposes, the self-shielded capsule is equipped with a kV tube with an X-ray supply, along with a kV imaging detector. Prior to activating the radiation beam, the imaging and monitoring subsystem takes images of the patient head and verifies that the tumor is in position (e.g., located at the isocenter). In case of a position discrepancy, the patient table automatically moves to compensate for the position discrepancy bringing the anatomical target into the system isocenter.

In some embodiments, in order to monitor patient position (and inferentially with respect to the LINAC, the imaging and monitoring subsystem includes an imaging radiation source fixed in a first shield component and a radiation detector affixed in a second shield component opposite the radiation source. In the embodiment described herein, the imaging radiation source is a kilo-voltage X-ray source and the imaging radiation detector is an amorphous silicon flat panel detector, although it is appreciated that any suitable imaging radiation source and detector could be used in other embodiments. During treatment, the subsystem obtains images of the patient anatomy episodically, determines patient movement, if any, and directs the patient table subsystem to adjust the patient position to position the tumor at the system isocenter as needed.

In one aspect, the imaging and monitoring subsystem is configured with a sequential view tracking methodology. The system performs imaging, in which at least two images are obtained sequentially from the imaging and monitoring subsystem to determine a position of the target. In the embodiments described herein, the kV tube and detector are used to acquire live patient image. In contrast, conventional systems, such as CyberKnife system or Brainlab system, use two sets of imaging devices for stereo image tracking. Stereo image tracking combines tracking results from each imaging system to form six degree of freedom results. To have a quick and accurate solution for patient alignment and tracking, the embodiments described herein utilize a moveable imaging subsystem to obtain sequential views from different perspectives toward the patients head. For example, the imaging radiation source can be used while the first shield component is at a first position to obtain a first image, and then the first shield component can be rotated to move the imaging device to a second position to obtain a second image from another perspective, the first and second images being used to determine alignment of the target with the isocenter. The system can be used in both initial patient alignment and tracking during delivery. While embodiments described herein include a single diagnostic radiation source, it is appreciated that in some embodiments, multiple sources at different locations on the first shield components could be used.

An exemplary imaging method utilizing sequential view tracking methodology can include the following steps:

1) Obtain first image at a first location of the diagnostic imaging system and correlate the X-ray image with digitally reconstructed radiograph (DRR) image to get accurate 2D translation (TX1 and TY1).
2) Move the diagnostic imaging system (typically by movement of a gantry or shield assembly on which the system is mounted) to at least a second location (can be a single axis motion, or combination of two axes), and correlate again to get second accurate 2D translation (TX2 and TY2).
3) Based on displacement matrix (i.e., rotation) between those two locations, combine two results (TX1/TY1, TX2/TY2) to calculate depth result of (TZ2).
4) Combine depth results (TZ2) with current location result (TX2/TY2) to form a 3D translation result (TX2/TY2/TZ2).
5) If any table motion happened between those two imaging locations, the displacement matrix (in Step 3) can also include table translation.
6) To get an accurate and robust TZ2 result, several approaches may be used:
    a. A minimal rotation angle reduces noise. (e.g. 20 degrees or greater, typically an angle between 40 and 70 degree, preferably about 60 degrees).
    b. A heuristics approach can be used to combine more than two images. For example, the sequential view results can be generated from the last image with all historical (previous, previous −1, previous −2, . . . ) images. Only the last few are used to avoid potential patient motion, and any outliers are removed to find the average results.
    c. An iterative approach can also be used between (3) and (4).
7) In addition to 3D translation result, 3D rotations can be calculated separately after initial position is close to the aligned position using coordinate descent or related optimization approach
    a. Search RotationX to find best match within a range (for example, −5 to +5), while fixing RotationY and RotationZ.
    b. Keep optimized RotationX, then search for optimized RotationY and
    RotationZ until new best values are found.
8) After initial rotations are found, optimization can be done, and steps 1 to 4 are optionally repeated for patient alignment.

G. MV Radiation Beam Monitor Subsystem

In another aspect, the system monitors the MV (therapeutic) radiation beam during treatment with a MV radiation beam monitor subsystem. The purpose is not to determine the position of the patient (as with the kV beam), but rather to verify and quantify the radiation intensity that passes through the patient. When captured after having passed through a patient (and knowing how much radiation was output by the LINAC), the residual radiation can be correlated with how much radiation the patient absorbed by comparing to the amount of radiation expected to be passed through the patient.

In some embodiments, the output of the MV radiation beam is measured by use of a MV radiation beam monitor subsystem that includes a scintillating membrane and one or more cameras that detect light from the scintillating membrane and output a corresponding signal. The resultant digitized signal is then processed through video signal processing electronics and fed into a system computing unit.

The system computing unit can then determine the dose data, beam profile data and the beam positioning data. One potential advantage of this embodiment is higher spatial resolution of the data since a high-resolution camera can be employed. A second advantage of this embodiment is simplicity and cost.

In some embodiments, the MV radiation beam monitor subsystem includes a removable MV radiation beam monitor unit, which is to be replaced before each treatment to ensure the MV radiation beam monitor performs properly and does not degrade with re-use. In some embodiments, the unit includes a removable MV detector camera with scintillating sheet. Typically, the scintillating sheet is made of phosphor $Gd_2O_2S$:Tb (GOS) on a silicone (PDMS) matrix and cast into a sheet. For every beam delivered, corresponding images are stored on the computer. The camera may be used a single time and replaced because the CCD camera degrades with MV radiation; a new factory-calibrated camera ensures accurate reading each time. The removable MV radiation beam monitor unit includes one or more coupling and/or alignment features to ensure consistently accurate spatial placement. The alignment features can include positive stops and positive locking mechanisms, for example, including magnets, latches, pegs, mortices or any suitable means. In some embodiments, the shield component in which the removable MV radiation beam unit is attached includes a contoured region that facilitates a desired placement of the unit or orientation, for example, the scintillating sheet being substantially perpendicular to the MV radiation beam. The contoured region is dimensioned to receive the removable unit and can include the positive stops and positive locking mechanisms therein to facilitate secure attachment of the removable MV radiation beam unit at a desired position, alignment and orientation. In addition to CCD, the imaging device include CMOS cameras, or any other digital imaging device.

A substantial deviation from expected dose to the measured dose will indicate an anomaly and the system will be shut down via the integrated control subsystem. This subsystem can include various inter-connect cables and other ancillary devices. Some of the ancillary devices include cameras and an intercom for the user to monitor and interact with the patient during the treatment. The system provides real time monitoring of the dose prescribed to the patient for each LINAC position. This monitoring feedback feature ensures that the treatment planning is delivered as prescribed and, in one embodiment is implemented with an MV imager that undergoes a change in response to absorbed radiation, and may be replaced with a new, factory-calibrated unit.

In some embodiments, the MV radiation beam monitor subsystem includes a removable single-use MV detector with silicon diode-based MV detector. In some embodiments, the single-use MV detector includes a scintillator and one or more photodiodes. Such a detector allows use of various techniques for in-situ radiation intensity measurement to quantify the quality of the treatment and provides data on in-situ positioning of the radiation beam, intensity distribution within the beam without the patient in the beam path, and residual beam with the patient in the beam path. The dose delivered for each site can be determined using this measurement for verification, with or without the patient in the beam path. The measured residual dose can be determined from a therapeutic beam detector unit and measured at multiple points. The theoretical value of the residual dose that is determined by the treatment planning system can be compared with a measured residual dose value using this technique for validation of the treatment and/or to assess treatment delivery quality. Validation or quality determinations can be recorded and used to adjust subsequent therapy delivery. In some embodiments, the output of the diode array is amplified, digitized and fed to a smart controller where the data is sorted and scaled and sent to an onboard system computer. The system computer with additional processing can be used to determine dose delivered data, the beam profile data, and beam positioning data. The LINAC that provides the high energy X-Rays, is modulated with a very small duty cycle (e.g. 500:1 duty cycle). Typically, the beam is only on for less than $1/300^{th}$ of the time (e.g. $1/500^{th}$ of the time), the rest of the time the beam is off; however, the time constant of the scintillator can be almost 3 orders of magnitude slower. The signal acquisition is synchronized with the on time of the radiation pulse to maximize the amount of signal to be read. This technique helps with the signal to noise ratio for low-level signals. In order to characterize the therapeutic radiation beam quality, spatial position and intensity measurements of the beam can be carried out. These values can be used to characterize the beam quality during the QA period of the system; can be used during the treatment to provide beam position and intensity distribution data, and can be used with a secondary dose measurement to validate actual dose delivered is desired and to quantify the quality of the treatment. For example, a residual dose measurement of the beam after passing through the patient can be used to compare with a calculated residual dose to validate the quality of the treatment. By analyzing the residual beam intensity distribution along with the CT data, one may be able to determine the positional accuracy of the beam with respect to the tumor during the treatment.

In one aspect, the MV radiation beam monitor subsystem includes a scintillator positioned incident to the high energy X-ray radiation such that the radiation excites the scintillator atoms that in turn produce emission of photons in the visible range. The visible light intensity is proportional to the radiation intensity. In some embodiments, a series of photodiodes are used to convert the visible light to electrical signals as an input to the system computer. The scintillator convers the radiation to visible light in the range of the photodiode's detection range. The photodiode array can be placed immediately after the scintillator to maximize the signal level and improve the signal to noise ratio. A number of diodes sufficient to cover the beam diameter should be used in order to provide a beam intensity profile measurement. There are various different photodiode array configurations that could be used. In some embodiments, the photodiode array utilizes 16 element diodes per chip and a sufficient number of chips to cover the entire beam using the largest collimator aperture. The electrical signal from the diode arrays are then amplified and digitized and fed to a computer. The computer software digitally processes the signal and produces dose measurement for validation during the treatment, as well as producing the beam intensity profile, and the XY position data. The XY positional data may be used to validate the accuracy of the beam's position on the tumor and to report possible errors.

Other light detection methods such a CMOS or CCD camera can also be used. In some embodiments utilizing CCD cameras, due to the small size of the camera's active area, such configurations typically use multiple optical components to project the image to the camera. The optics typically require that the CCD cameras be placed some distance away from the scintillator to allow room for focusing. The signal intensity received by the CCD camera is calibrated to a known radiation intensity, thereby compensating for any loss of light occurring in the interposed distance between scintillator and CCD.

II. DETAILED EXAMPLES

FIG. 1 illustrates an overview of an exemplary self-shielded treatment system, which includes the mechanical subsystem, the largest piece of hardware in the system. The system includes a shield that includes two movable shield components, oblique shield 101 and axial shield 105 oblique shield 101 rotating on oblique axis 130 and axial shield 105 rotating on axial axis 135. Upon rotation of axial shield 105, both axial shield 105 and oblique shield 101 are rotated about axis 135, while oblique shield 101 is independently rotatable about an oblique axis 130 that is transverse to the axial axis 135. Patient 150 is lying within the apparatus on a patient table (not shown) substantially aligned along axial axis 135 with target at isocenter 136 located at intersection of axial axis 135 and oblique axis 130. Mounted on the inner surface of oblique shield 101 is LINAC 110 that produces MV radiation therapy beam 145 that passes through patient 150 and received by MV radiation detector 115 also mounted upon the inner surface of oblique shield 101. Mounted upon the internal surface of axial shield 105 is KV radiation emitter 120, which is used for real-time X-ray image-based position sensing by passing its beam 140 through patient 150 to kV radiation detector 125 mounted on the internal surface of oblique shield 101. It is noted that the shield components depicted are of solid construction and hatch lines have been omitted merely for clarity.

Figure 2A:
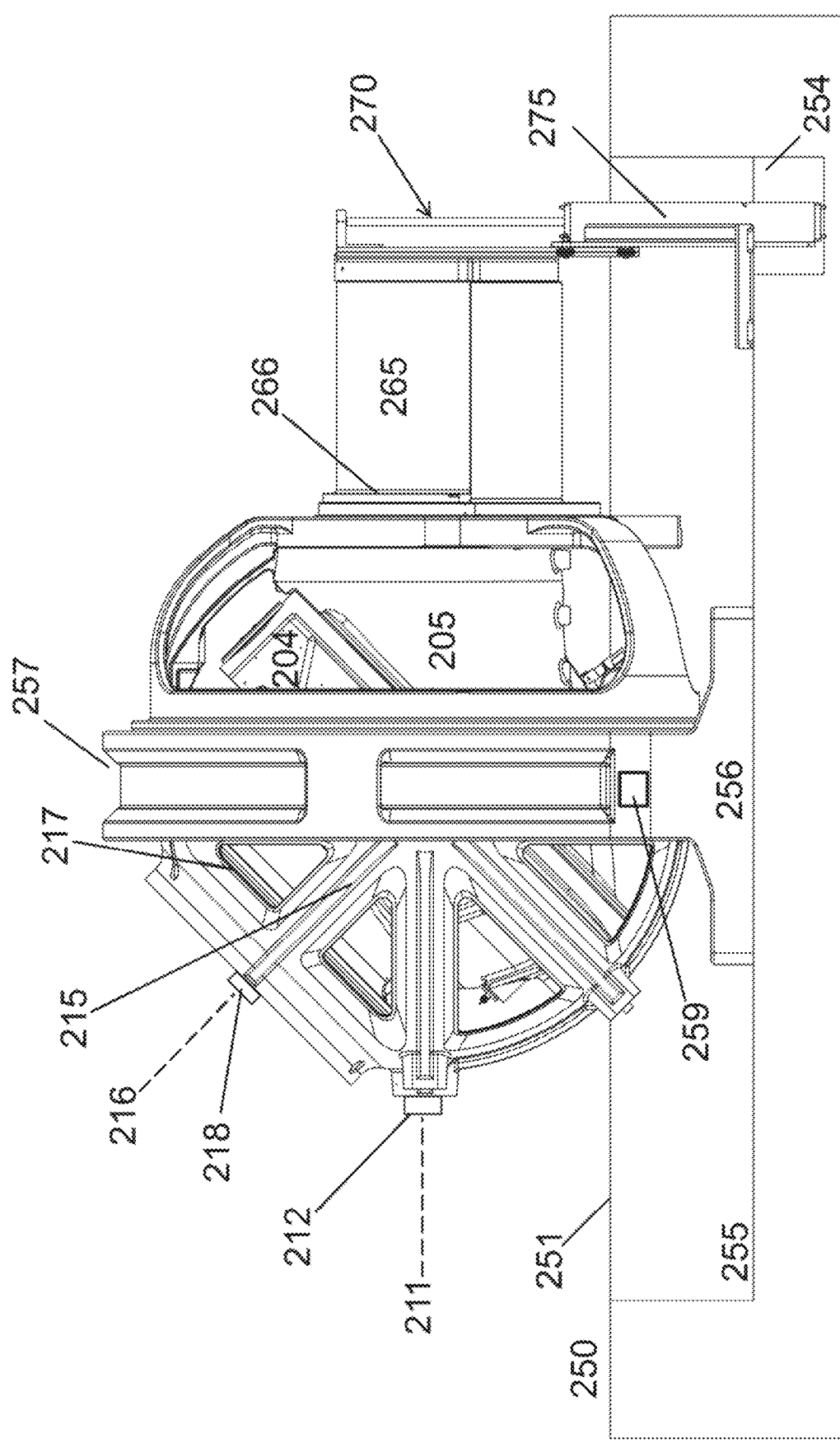
FIG. 2A shows a side view of the system and interface with a supporting base ring and patient table in accordance with some embodiments.

FIG. 2A shows the mechanical subsystem of the treatment system in greater detail as viewed from the side. In this embodiment, the subsystem is housed in a floor pit, although it is appreciated that the subsystem could also rest on a floor surface without a pit assuming sufficient overhead clearance. The axial axis 211 turns via the axial bearing assembly (not visible as it is obscured by base ring) with multichannel electrical and electronic supplies rotationally commuted by axial slip rings 212. Axial shield 205 turns on axial axis 211 around the torso of the patient within. Oblique axis 216 turns on oblique bearing assembly 217 with multichannel electrical and electronic supplies rotationally commuted by oblique slip rings 218. Oblique shield 204 is covered by and enclosed with system electronics by oblique support bracket 215. Shell 265, which rotates on shell bearing 266, covers and shields the entry portal from above the patient table base 260 when the system is in the closed, shielded configuration. Portal is the entryway into the interior of the device that encloses the upper ⅔ of the patient table when door 275 and shell 265 are in the closed and shielded configuration.

In this embodiment, the treatment system sits within a formed concrete pit 255 approximately two feet deep. The pit serves as additional radiation shielding for the lower portion of the device, and advantageously places the patient bed (not shown here) at a comfortable height for seating and bringing patients in and out of the device to the floor level. The pit also reduces the ceiling height required for the apparatus in the room, and makes the apparatus more aesthetically appealing by appearing smaller. Portions of the pit not occupied by the apparatus itself can be covered by flooring 251 that meets the normal floor level 250 of the apparatus. The entire mechanical apparatus is held together chiefly by a strong central base ring 257 which is anchored to the concrete at the bottom of pit 255 with ring base 256 and balances the weight of oblique shield 204 and axial shield 205 and other massive components of the system. It is appreciated that ring base 256 can be an integral portion of base ring 257, as shown here, or can a separate component attached thereto. A deeper extension of the pit 254 accommodates the vertical travel needs of door 270 at its fully opened position.

In this embodiment, the treatment system includes proximity detectors 259 disposed near the base on each side to detect proximity of a person so as to effect an automatic shut-off of radiation and motion upon unauthorized entry of a person into an immediately surrounding zone so as to prevent unintended exposures to radiation or contact to moving system parts during treatment. In some embodiments, the proximity detector has a detection range of at least 180 degrees, typically up to 270 degrees such that one proximity detector on each side of the treatment system effectively covers a zone extending around the entire system. Alternatively, a single proximity detected with a 360 degree range could be positioned above the entire system. The area covered by the proximity detectors can be marked by a boundary. Such a configuration can allow the area outside the boundary to be an uncontrolled area since there is little risk of unintended exposure since the system will shut off if the boundary is crossed.

Figure 2B:
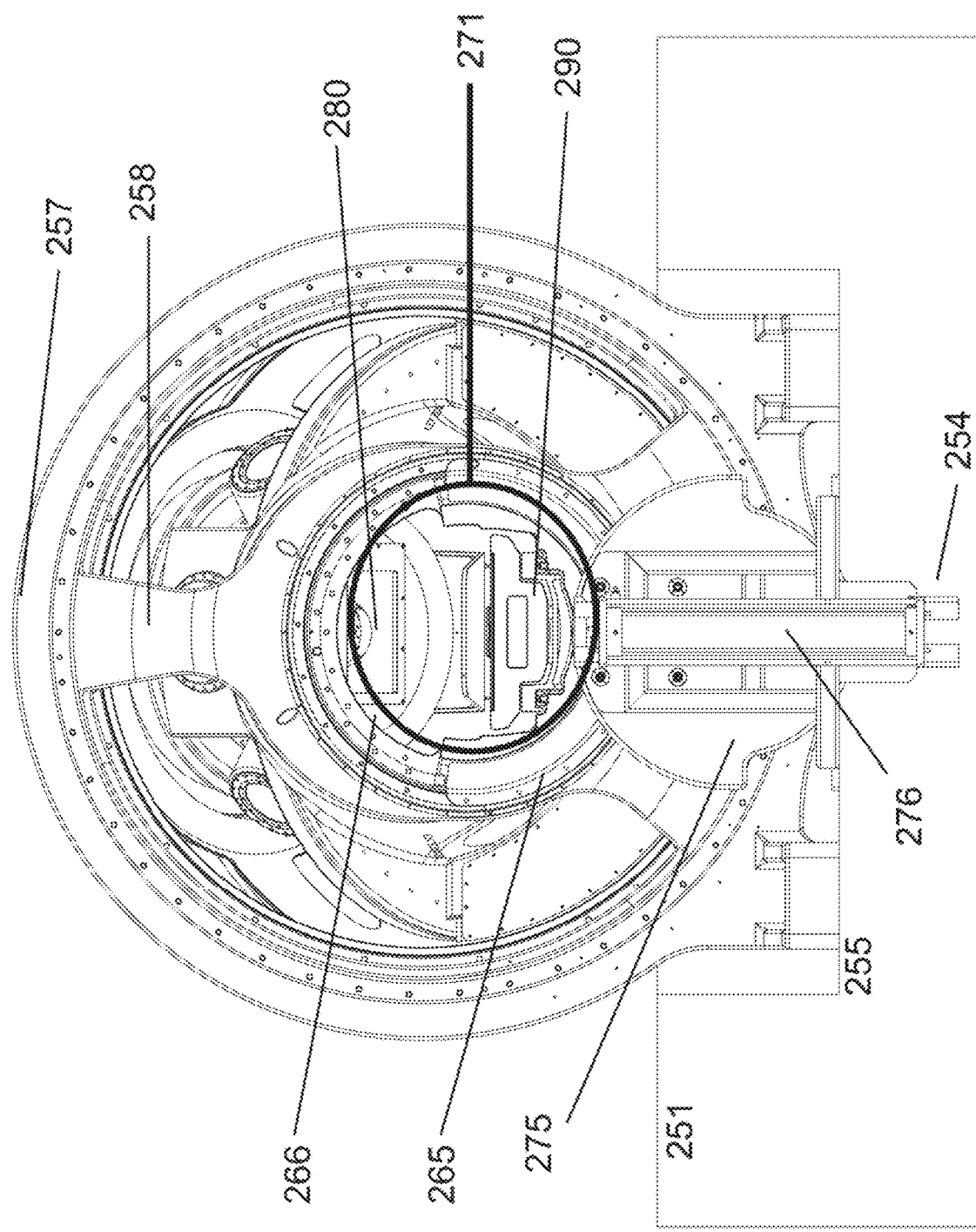
FIG. 2B shows a front view of the system with an open patient portal in accordance with some embodiments.

FIG. 2B shows a view of the mechanical subsystem as viewed from the front. Door 275 is vertically lowered to an open position thereby revealing portal opening 271. Through portal opening 271, collimator 280 and patient table 290 are visible within the interior. In this embodiment, door 275 is opened by lowering it into pit extension 254, using the door mechanism including door actuator 276 (e.g. a hydraulic jack) and using the space provided by this yet deeper portion 254 of pit base 255. Such a configuration is advantageous as it reduces the clearance required around the portal opening for the door and associated movement mechanisms. It is appreciated that in various other embodiments, the door can be lowered from above or could be translated or rotated into position from any direction.

In this embodiment, the entire mechanical superstructure is linked together and supported by base ring 257, which substantially balances the massive loads of heavy shielding and other equipment on either side. Axial bracket 258 covers the axial shield and serves to cover essential electronics in a manner analogous to the oblique bracket on opposite side of the machine (not shown). Note that shell 265 is in the open position, where it has rotated about shell bearing 266 to underlie patient table base below patient table 290, leaving patient table 290 exposed from above. This position allows the patient table to roll outward to its full extent, enabling patients to be loaded and unloaded from the apparatus. Upon loading, patient table 290 rolls toward the collimator, shell 265 rotates about shell bearing 266 until the shell covers patient table 290, and door 275 on door actuator 276 raises into the closed and shielded position.

Figure 3:
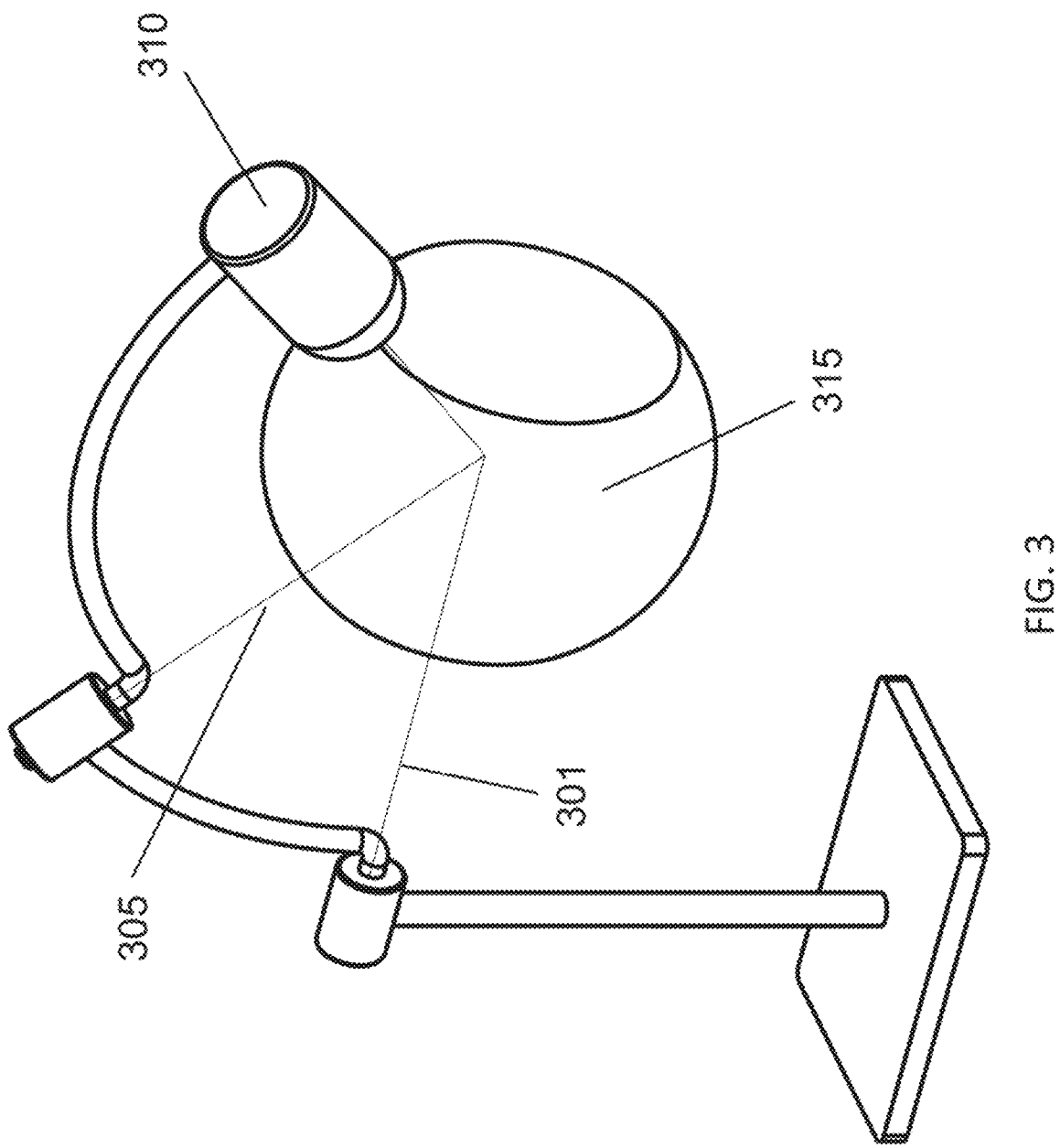
FIG. 3 schematically illustrates the axes of movement of the mechanical subsystem and their relationship to one another in a simplified paradigm in accordance with some embodiments.

FIG. 3 schematically illustrates the axes of movement of an exemplary mechanical subsystem and their relationship to one another in a simplified paradigm in accordance with aspects of the invention. Axial axis 301, in the system, controls movement of a first shield component (e.g. axial shield). Oblique axis 305, in the system, controls independent movement of a second shield component (e.g. oblique shield). The shield components have been omitted to better illustrate their range of movement provided by their respective axes. In this embodiment, LINAC 310 is coupled to the oblique axis 301 via the associated oblique shield, such that LINAC 310 is capable of irradiating targets within potential treatment volume 315. As can be seen the potential treatment volume 315 is a substantially spherical shape about the isocenter (not shown). It is appreciated that, in this embodiment, oblique axis 305 may move independently of axial axis 301, but movement of axial axis 301 necessarily results in movement of oblique axis 305 about axial axis 301. Although this configuration provides considerable range of movement of the treatment beam to the target, there is a portion of the treatment volume 315 located distally of axis 301 that the LINAC cannot reach. Optionally, this portion can be effectively reduced by use of a patient table that can move the target along one or more axes to the accessible portion of the treatment sphere. An example of such a patient table is described in further detail below. In some embodiments, each of the axial shield and the oblique shield are rotatable 360 degrees about their respective axes of rotation. It is appreciated however, that this range of rotation of each shield component is not required to maintain full range of movement of the treatment beam, for example, one of the shield components can be rotatable by only 180 degrees so long as the other shield component is rotatable by 360 degrees.

Figure 4:
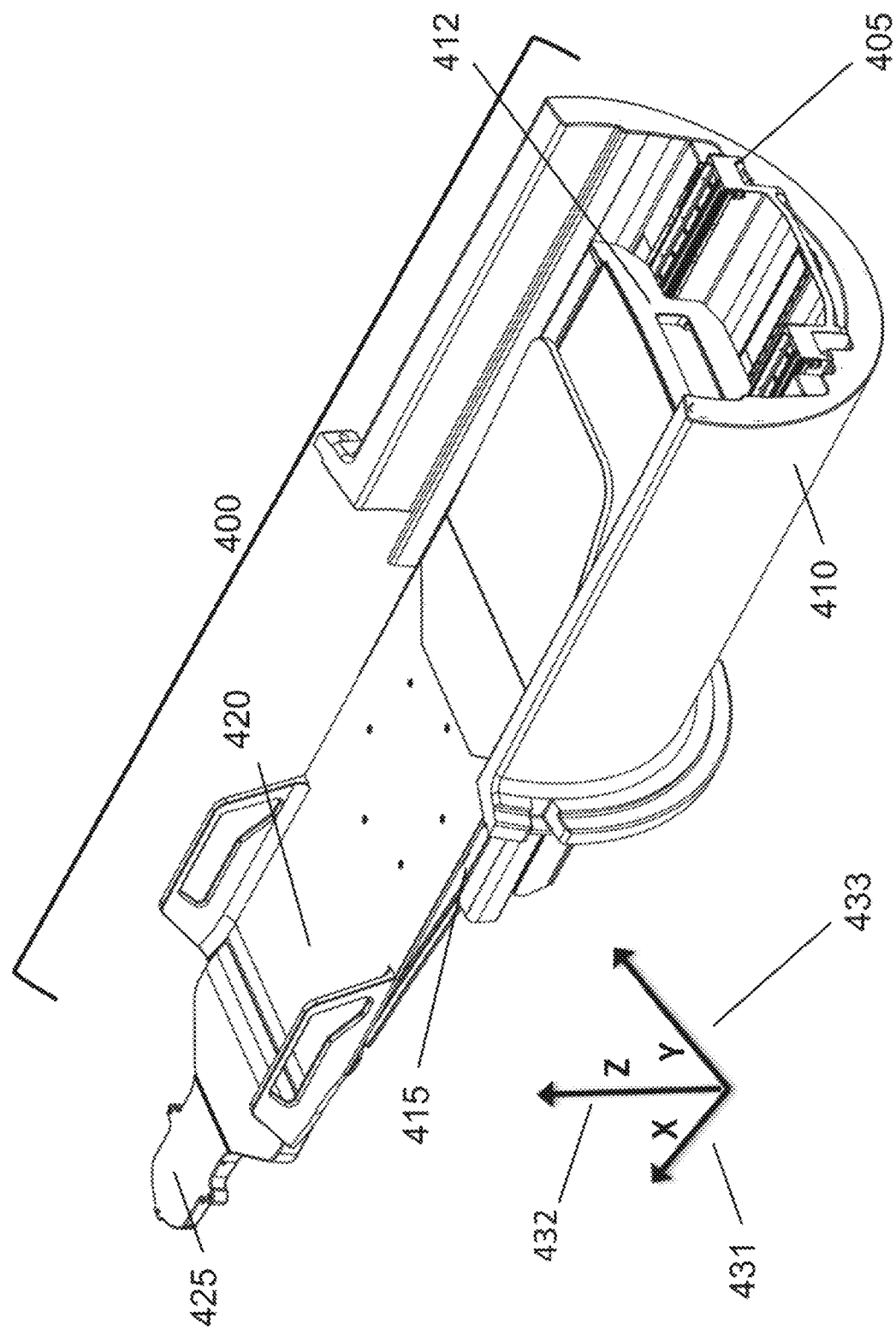
FIG. 4 shows a patient table and associated axes of motion in accordance with some embodiments.

FIG. 4 shows an example patient table and its axes of motion in accordance with aspects of the invention. Patient table 400 supports and positions the patient for correct MV radiation beam aim during treatment. Patient table 400 has two y-axes 431 of motion, a pitch motion around the x axis 433, and a yaw motion around the z axis 432. Lower cart 405 moves along the y-axis 431 of table base 410, as does upper cart 412. Pitch plate 415 rotates around the pitch axis, which is parallel to x-axis 433, in a pitch fashion by raising or lowering the head end of the patient bed 420 along z-axis 432. The patient bed 420 rotates about the yaw axis, which is perpendicular to the x-axis, in a yaw fashion by moving the head of the patient bed left or right along x-axis 433. The patient bed has headrest portion 425 that includes facets for attaching a radiosurgical stabilizing face mask. Optionally, the headrest 425 can include an additional pitch joint that can be automatically moved so as to move the target so as to increase the accessible portion of the treatment sphere. Typically, the additional pitch joint is configured to allow headrest 425 to pitch between a 30 degree incline and decline, so as to further reduce the inaccessible portion of the treatment sphere. The associated movement of each table component are described further below and depicted in FIG. 5

Figure 5:
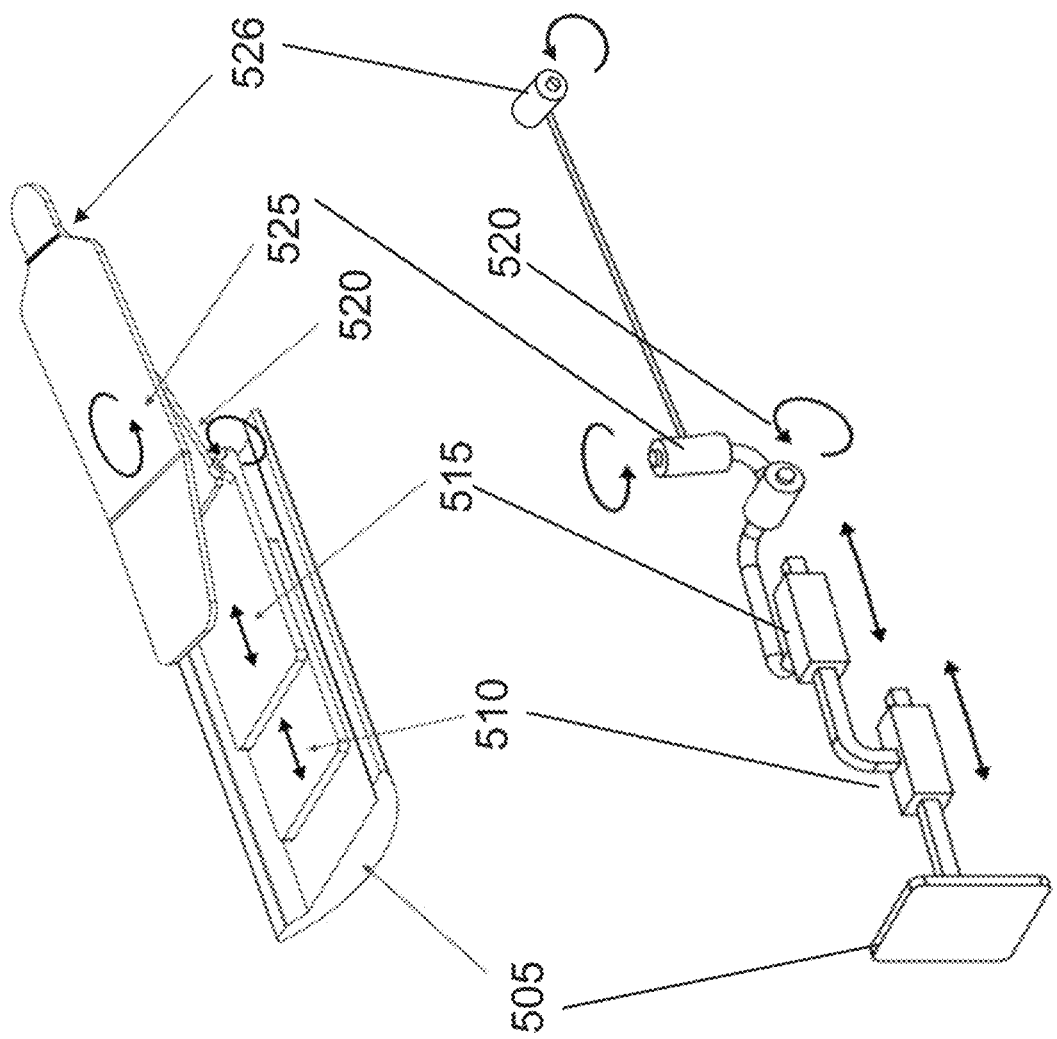
FIG. 5 shows the moveable layers of the patient table and axes of motion along with a simplified model of the respective axes in accordance with some embodiments.

FIG. 5 shows the example patient table of FIG. 4 with the associated axes of motion along with a simplified model of those axes. Table base 505 supports the x-axis translation movement of the table. Lower cart 510 rolls in a first x-axis translational motion. Upon lower cart 510 rolls upper cart 515 for a second x-axis translational motion. Pitch plate (pitch rotation) 520 is moved in a pitch motion, being affixed at the portion that accommodates the patient's buttocks, and free to move in pitch fashion at the end that accommodates the patient's head. The patient bed 525 also rotates in a yaw fashion. Headrest 526 pitches along a pitch axis. This configuration of movable components of the patient table facilitate positioning of the patient through the entry portal and positioning of the target within the patient (e.g. patient's head) within the treatment space within the movable shields. While a particular configuration of table components and associated joints are depicted here, it is appreciated that alternate configurations of joints could be utilized to provide the same or similar range of movement in accordance with the invention.

Figure 6:
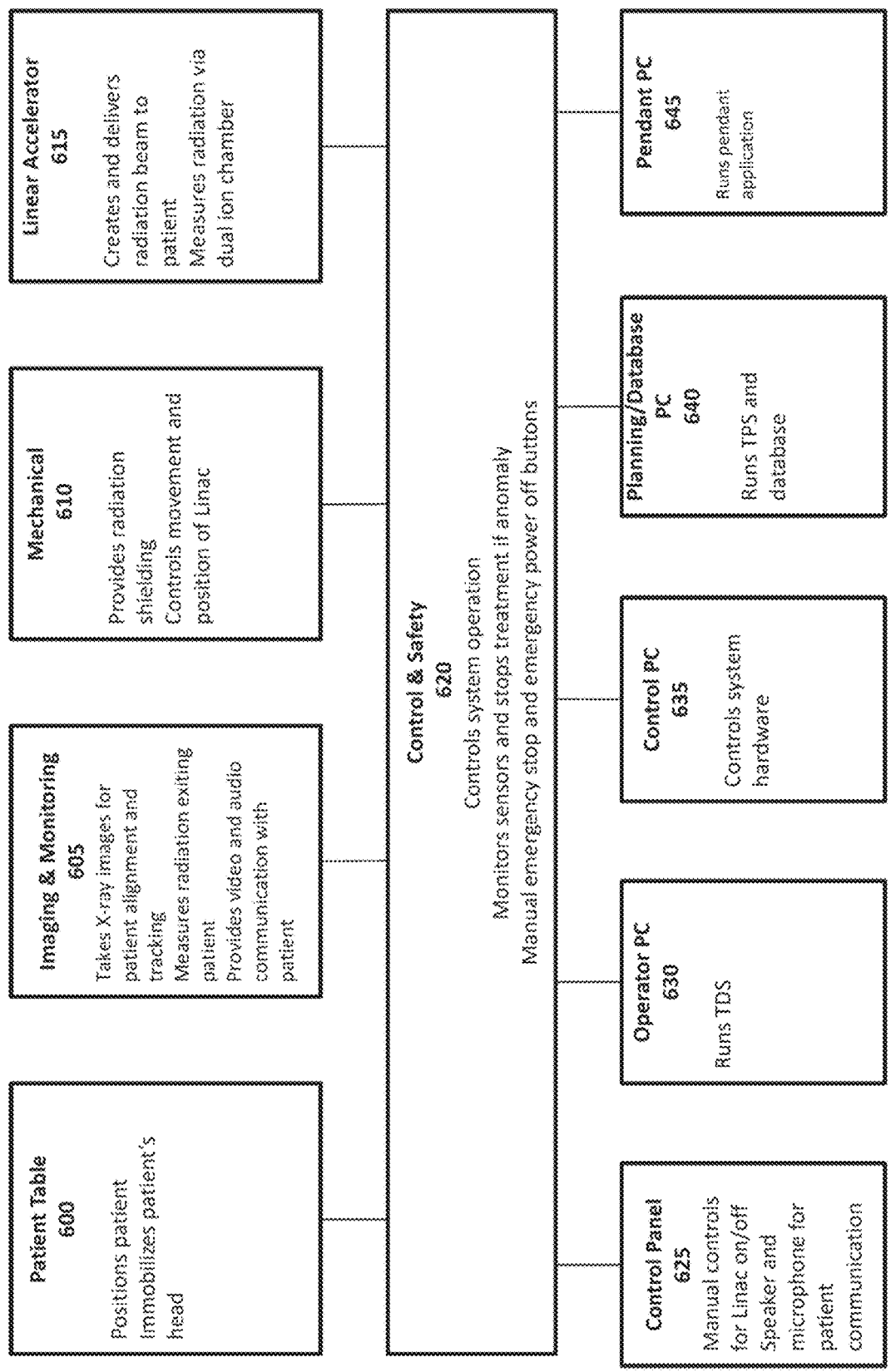
FIG. 6 illustrates the integrated control subsystem that monitors and controls all hardware and software subsystems in accordance with some embodiments.

FIG. 6 illustrates an example main integrated control system that monitors and controls all hardware and software systems of a treatment system in accordance with aspects of the present invention. Patient table 600 serves to position patient and immobilize the patient's head in the correct position so that the tumor is isocentric, and is networked to the control and safety subsystem 620. Imaging and monitoring subsystem 605 obtains diagnostic images (e.g. obtains kV X-ray images for patient alignment and tracking) and performs monitoring and/or verification of the treatment radiation beam (e.g. measures MV radiation exiting the patient). This subsystem can also provide video and audio communication with the patient. Subsystem 605 can be networked to control and safety subsystem 620. Mechanical subsystem 610 provides radiation shielding and controls movement and position of the LINAC and can be networked to control and safety subsystem 620. LINAC subsystem 615 creates the MV radiation beam and delivers it to the patient, with internal output measurement provided in the dual ion chamber, and can be networked to control and safety subsystem 620. Control panel 625 provides manual controls for LINAC on/off function, speaker and microphone for patient communication and other functions, and can be networked to control and safety subsystem 620. Operator PC 630 runs the treatment delivery subsystem and can be networked to control and safety subsystem 620. Control PC 635 controls system hardware and is networked to control and safety subsystem 620. Planning and database PC 640 runs the treatment planning subsystem and associated database and can be networked to control and safety subsystem 620. Pendant PC 645 runs pendant application and is networked to control and safety subsystem 620. It is appreciated that the above systems can be networked to the control and safety subsystem by hardwired connections or through a wireless network.

Figure 7:
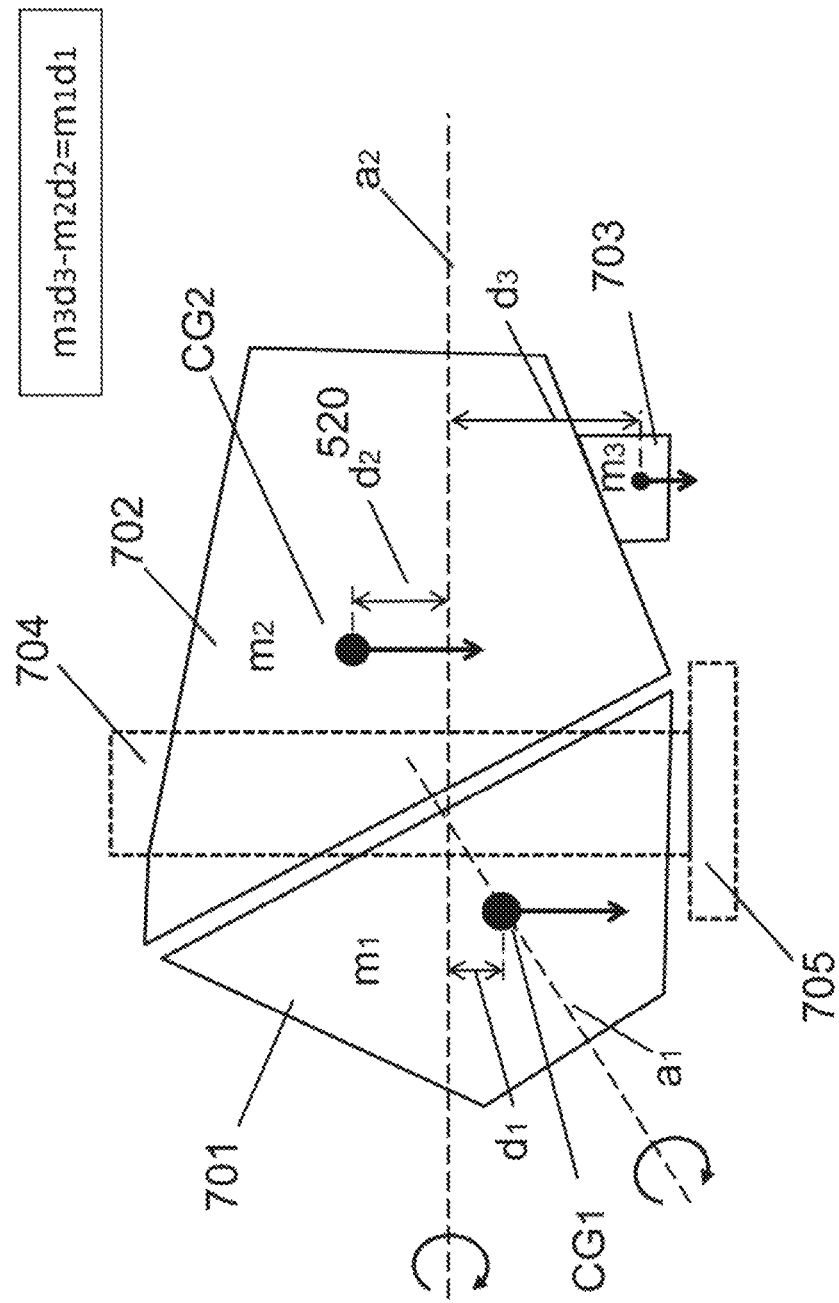
FIG. 7 schematically illustrates the movable shield components of a self-shielded system in accordance with some embodiments.

FIG. 7 is a schematic illustrating the balancing of the weight distribution of the axial shield and oblique shield of the radiation shield. Axial shield 702 rotates about axis $a_2$ and is movably interfaced with oblique shield 701 such that rotation of the axial shield 701 also rotates the oblique shield about axis az. Given the differing geometries and distribution of mass of the axial and oblique shields, the rotation of the radiation shield would typically require relatively large, oversized motors in order to accommodate the substantial variations in reaction forces during a single rotation of the shield. To avoid these variations, one or more counterweights can be mounted on the respective shield components in order to distribute weight more uniformly about the axis about which each rotates. In this embodiment, the oblique shield component is balanced around the oblique axis about which it rotates and the axial shield and oblique shield assembly are balanced around the axial axis about which the assembly rotates. In turn, the axial and oblique shields can be counterbalanced about a common support, base ring 704 that extends around the radiation shield assembly and includes a lower base portion 705. FIG. 7 shows the center of gravity $CG_1$ of the mass $m_1$ of oblique shield 701 balanced around the oblique axis, which is offset from the axial axis $a_1$ by distance $_{d1}$. The center of gravity $CG_2$ of the mass $m_2$ of axial shield 702 is offset from the axial axis $a_2$ by a distance of $d_2$. Therefore, to balance the shield assembly about the axial axis $a_2$, a counterweight 703 of $m_3$ is mounted to the axial shield 702 at a distance of $d_3$ from the axial axis, according to the equation: $m_3d_3-m_2d_2=m_1d_1$. While only one counterweight is shown in this example, it is appreciated that such balancing can include additional counterweights mounted on the various shield components as needed. Such an approach of counterbalancing the shield components and shield assembly about their respective axes of rotation reduces the motor requirements needed to rotate the shield components as described herein, thereby reducing the overall size and footprint of the device as well as reducing cost and complexity of the mechanical drive system.

As shown, the axial and oblique shields counterbalance each other about the common support ring. Typically, the central base support ring is disposed vertically substantially between the centers of mass, although in some embodiments, the central base support ring can be coincident with the centers of mass or extend a distance beyond. In one aspect, the angled interface between the axial shield and oblique shield (e.g., 45 degrees) allows the centers of mass to be relatively near each other, which allows the slew drive ring that rotates the shield assembly drive by one or more linear motors to be centrally located on support ring 704.

Figure 8:
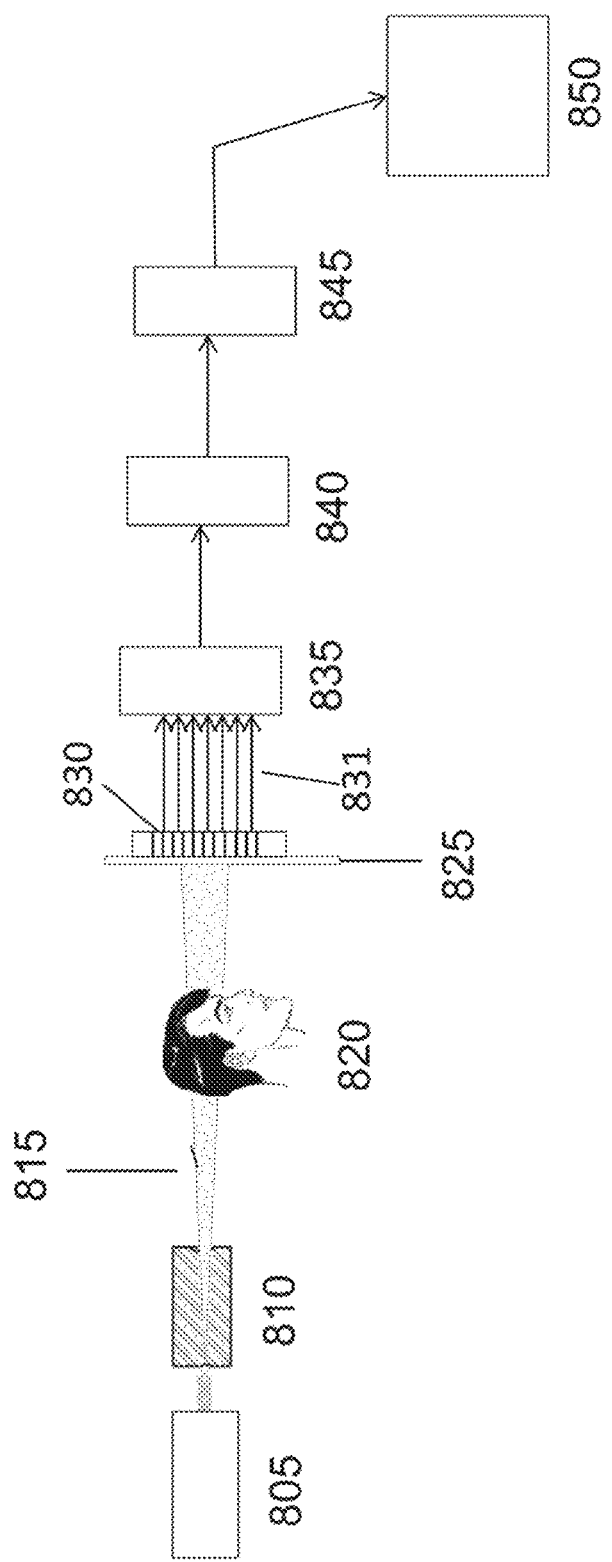
FIG. 8 illustrates a system by which the MV radiation that has passed through a patient onto a scintillating sheet is captured by a photodiode array with the resulting signal processed and stored in accordance with some embodiments.

FIG. 8 illustrates an embodiment that includes a MV therapeutic radiation monitoring or verification subsystem in which the MV therapeutic radiation having passed through a patient onto a scintillator is captured by a photodiode array with the resulting signal processed and registered in the system computer. In this embodiment, LINAC 805 emits MV therapy radiation beam 815, which passes through collimator 810 and then through the targeted portion of patient 820. The remaining radiation beam then strikes scintillator 825, which glows with visible light at an intensity proportional to the intensity of radiation beam 815. The glowing of scintillator 825 is transduced by photodiode array 830 into electronic signals 831 from those component photodiodes. The signals are passed collectively or in segregated form through amplifier 835, analog-to-digital converter 840, and then to signal processing computers 845. The resultant processed signal is then sent to system computing unit 850. This process occurs continuously during the treatment session, thereby verifying the total amount of radiation received over the session. In some embodiments, a beam stop (not shown) is placed directly in the MV radiation beam's path immediately after the scintillating sheet or diodes.

Figure 9:
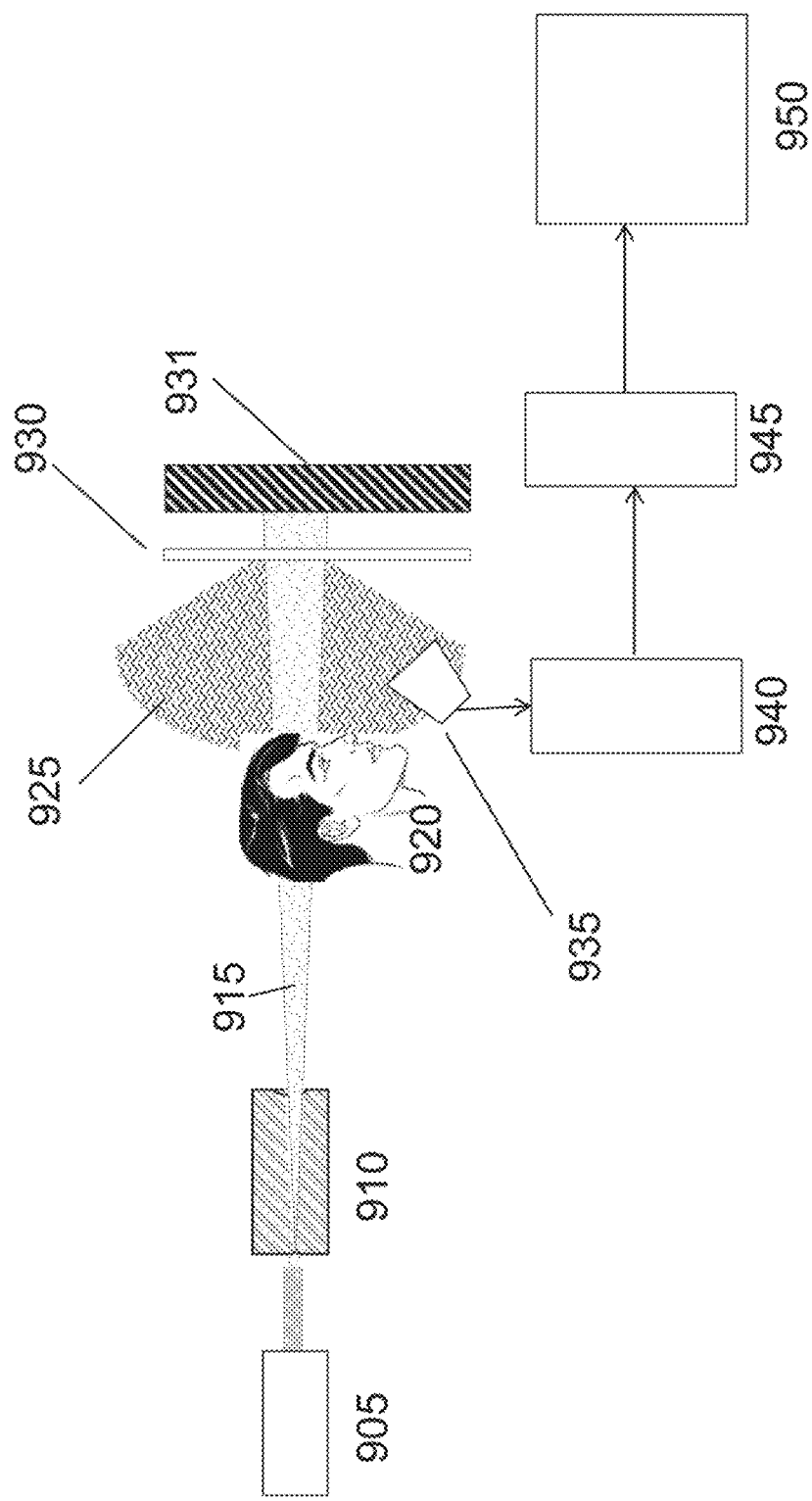
FIG. 9 illustrates means for verifying the amount of radiation that has passed through the patient by capturing the fluorescence from a scintillating sheet using a CCD camera in accordance with some embodiments.

FIG. 9 illustrates another embodiment with an alternate means for verifying the amount of radiation that has passed through the patient by capturing the fluorescence from a scintillating sheet using a CCD camera. In this embodiment, LINAC 905 outputs MV therapy radiation beam 915, which passes through revolving collimator 910 and to the targeted region of the head of patient 920. After passing through patient 920, MV radiation beam 915 strikes scintillator 930. In response to being struck by MV radiation 915, scintillator 930 produces visible fluorescent light 925 that is proportional to the intensity of the radiation beam. Fluorescence 925 is captured by CCD camera 935, which outputs a signal with image information. The image information is then passed in real time to video data acquisition electronics 940, video signal processing electronics 945, and ultimately passed to system computing unit 950 which documents and certifies that the amount of radiation treatment that the patient has received. Because the fluorescence captured by CCD camera 935 reflects radiation that has already passed through the patient, the system computing unit 950 can receive a more accurate assessment of the radiation received by the patient than in systems in which the radiation intensity measurement is done prior to passing the beam through patient 920. It is appreciated that this approach can be used in place of or as a supplement to an intensity measurement performed prior to passing the beam through the patient. In various embodiments, this process occurs continuously during the treatment session, thereby verifying the total amount of radiation received over the session. In some embodiments, beam stop 931, typically a piece of thick shielding, is placed directly in the MV radiation beam's path immediately after the scintillating sheet or diodes. Beam stop 931 ensures that the high-intensity radiation in that location is not transmitted externally of the shielded apparatus.

Figure 10:
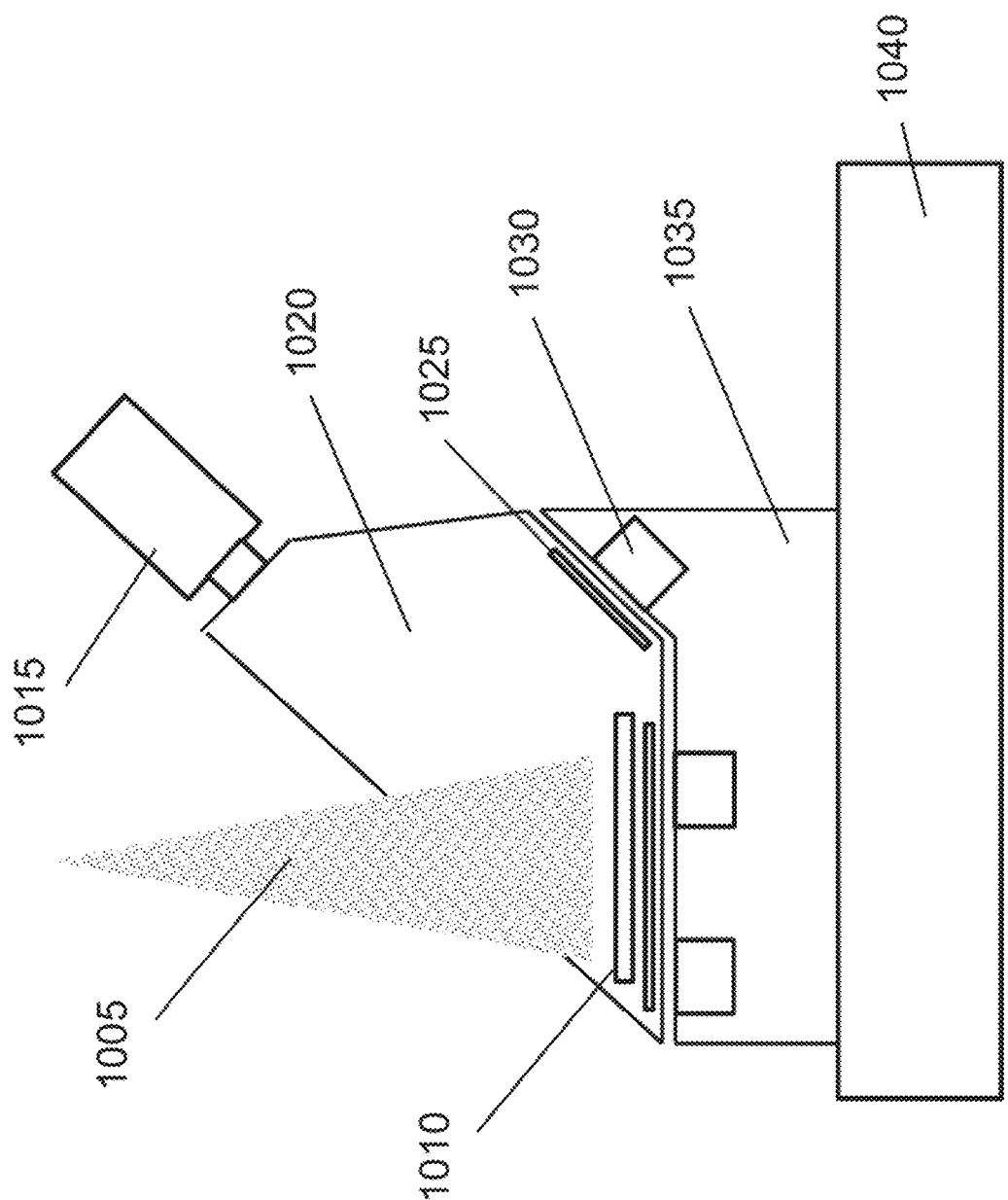
FIG. 10 illustrates a specific embodiment of the general scintillator with CCD capture as described in FIG. 9, but here in the form of a hardware unit containing both the scintillating sheet and CCD camera that is removed and replaced in precise intended position between each patient use.

FIG. 10 illustrates a removable and replaceable scintillator/camera combination for use with treatment system in accordance with aspects of the invention. Preferably, this is a consumable piece of hardware containing the scintillating sheet and CCD camera that is removed and replaced between each patient use, insuring that a freshly calibrated CCD camera is used every time for the most accurate possible readings delivered to the treatment verification system and associated database record. Removable housing 1020 has affixed scintillating sheet 1010 and affixed CCD camera 1015, and thus may be removed as a unit and replaced. Since radiation degrades the CCD camera over time, more accurate MV detection can be achieved by replacing the unit between radiosurgical treatments. Housing 1020 may be positively affixed to mounting base 1035 by one or more removable coupling features. In some embodiments, the one or more coupling features are configured to ensure a proper alignment and/or orientation of the unit within the interior of the shield so as to provide consistent, reliable monitoring and verification of the therapy beam. The one or more coupling features can include any suitable means of coupling, which may include: pegs and mortices, latches, and as shown in FIG. 10, magnets 1030 that are attracted to precisely placed ferrous metal tabs 1025. Mounting base 1035 can be affixed to the shielded wall 1040 of the mechanical subsystem within the MV radiation beam's path. Florescent visible light captured by CCD camera 1015 is proportional to the high-energy (MV) x-ray beam intensity. Since a new factory-calibrated CCD camera is in each removable housing 1020 and used with each patient, the highest treatment verification standards are maintained.

III. IMAGING AND TRACKING METHODOLOGY

Figure 11:
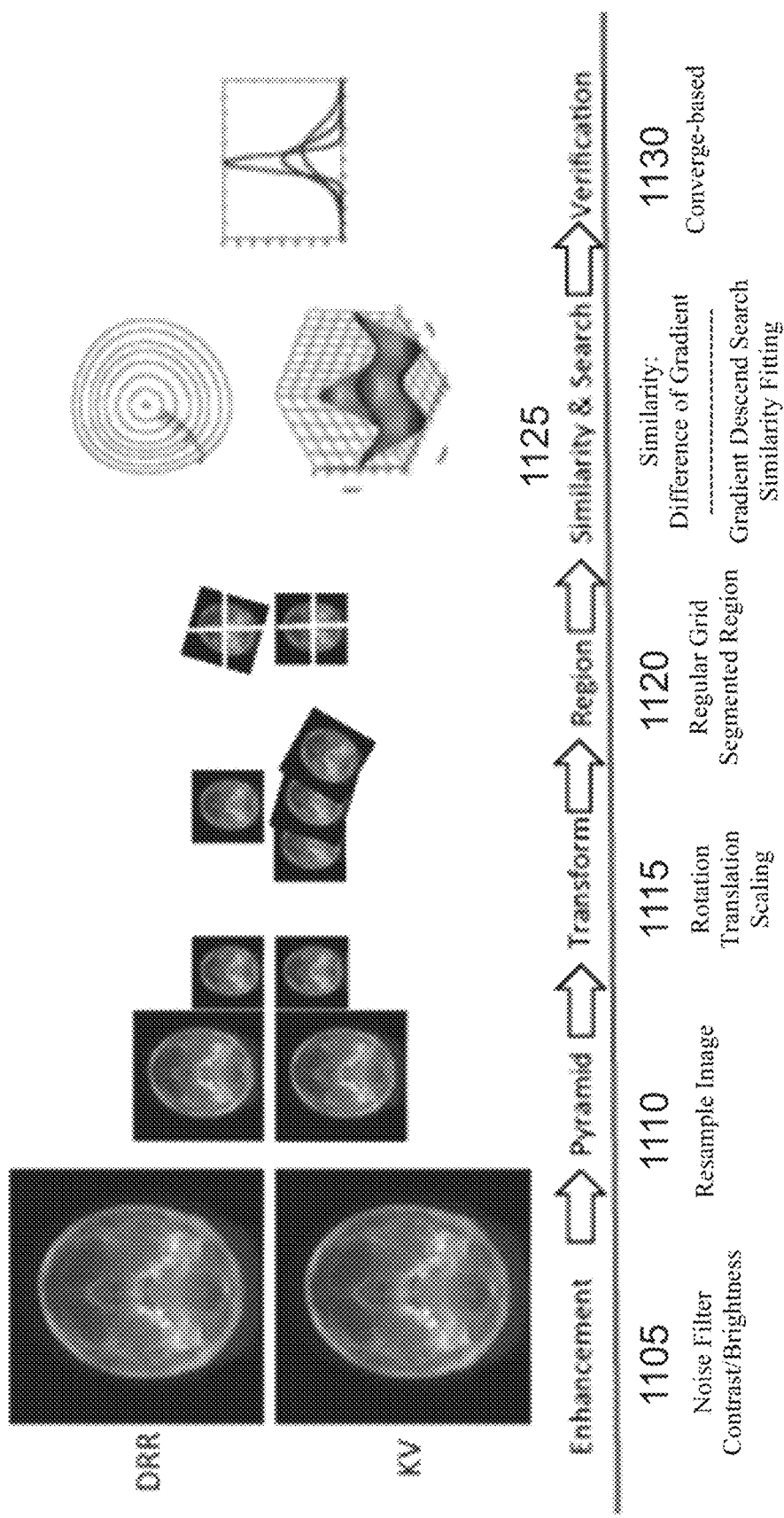
FIG. 11 illustrates tracking methodology framework for sequential view imaging in accordance with some embodiments.

FIG. 11 illustrates an exemplary tracking methodology framework. In some embodiments, the tracking method includes enhancement 1105 of kV and DRR images in parallel. Enhancement can include use of noise filters, contrast and brightness, etc. Next, pyramid resampling of image 1110 can be used to enable efficiency of the process by permitting the system to work on lower resolution images first to remove noise and local minima, but can return to full resolution in the final step. Next, the method can transform the images 1115, which can include rotation, translation, and scaling. Then, the images can be segmented into regions 1120 on a regular grid. Segmenting into regions serves to exclude unwanted parts of the image such as moving parts of the skull (e.g. jaw) that can reduce accuracy over overall pattern matching. Next the method can conduct similarity measurement and search assessment 1125. Similarity can be assessed using difference of gradient and can further utilize a gradient descent or coordinate descent optimization method with similarity curve fitting. Lastly, the method can include verification 1130, which can be based upon convergence.

Figure 12:
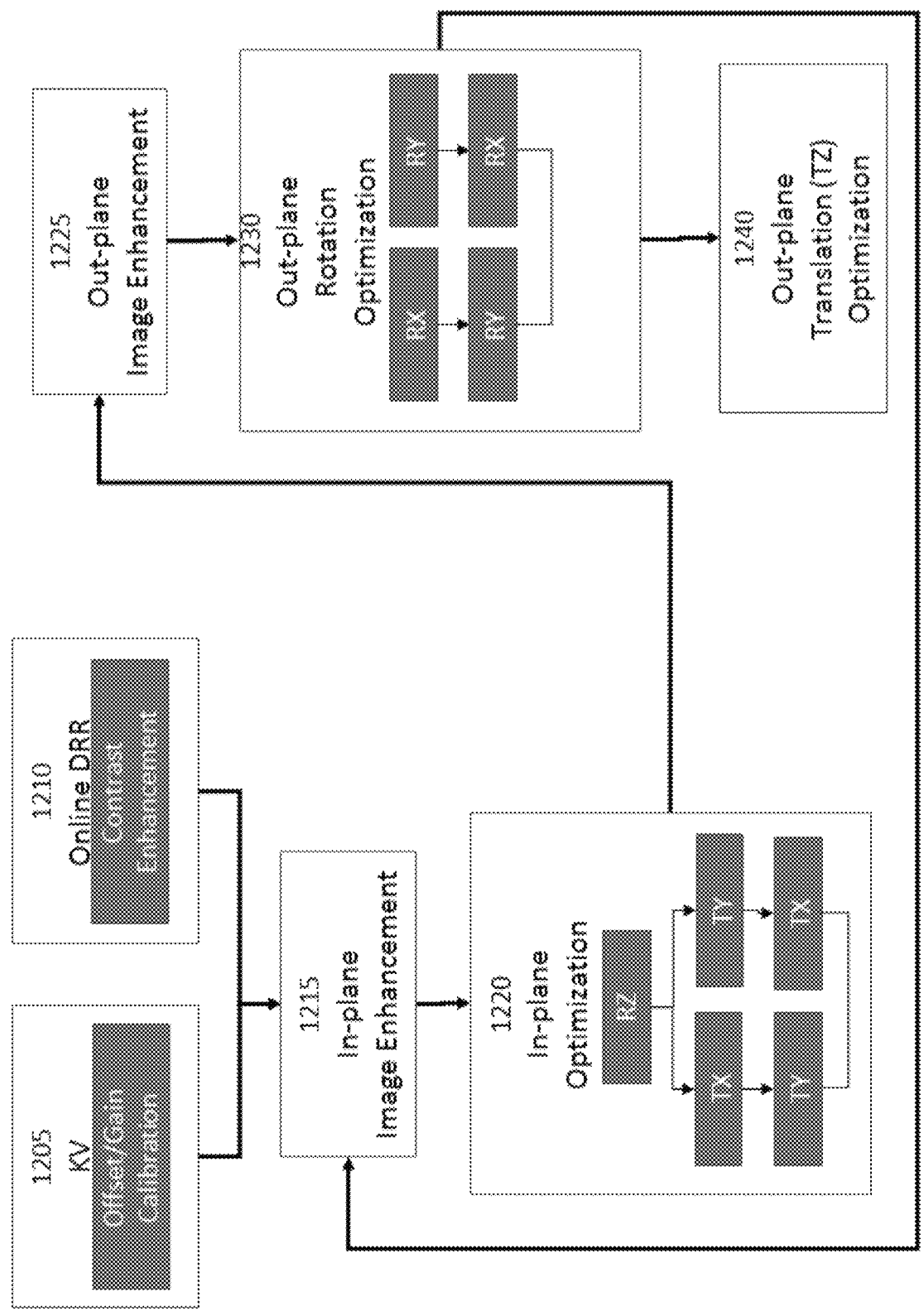
FIG. 12 illustrates a 6D tracking methodology optimization process flow in accordance with some embodiments.

FIG. 12 is a process schematic for optimization of tracking. In step 1205, kV images are acquired from the imaging and monitoring subsystem. After the raw images are acquired, offset and gain calibration are performed to get uniform intensity and remove detector artifacts, such as bad pixels. In step 1, real-time digitally reconstructed radiograph (DRR) images are generated based on system geometry and target location. After 2D DRR images are generated, some image enhancement steps, such as contrast enhancement, can be used to emphasize certain features. This step can require extensive calculation, and can be accelerated by GPU. In step 1215, image enhancement approaches are used for in-plane transformation estimation. In-plane transformation includes two in-plane translations, and one in-plane rotation. In step 1220, algorithm uses coordinate descent approach to find the optimized solution of in-plane parameters. For example, algorithm can find in-plane rotation (RZ) first, then find TX and TY, or find TY first and then TX. The final optimization transformation, including RZ, TX and TY are found. In step 1225, image enhancement approaches are used before out-plane transformation estimation. Out-plane transformation include two out-plane rotations, and one out-plane translation. Due to weak signal of depth features, out-plane enhancement may be different than in-plane enhancement as described in step 1215. In step 1230, the algorithm uses coordinate descent approach to find out-plane rotations RX and RY. Either search RX first or search RY first. In step 1240, the last step of algorithm is to optimize out-plane translation (e.g., depth).

Figure 13:
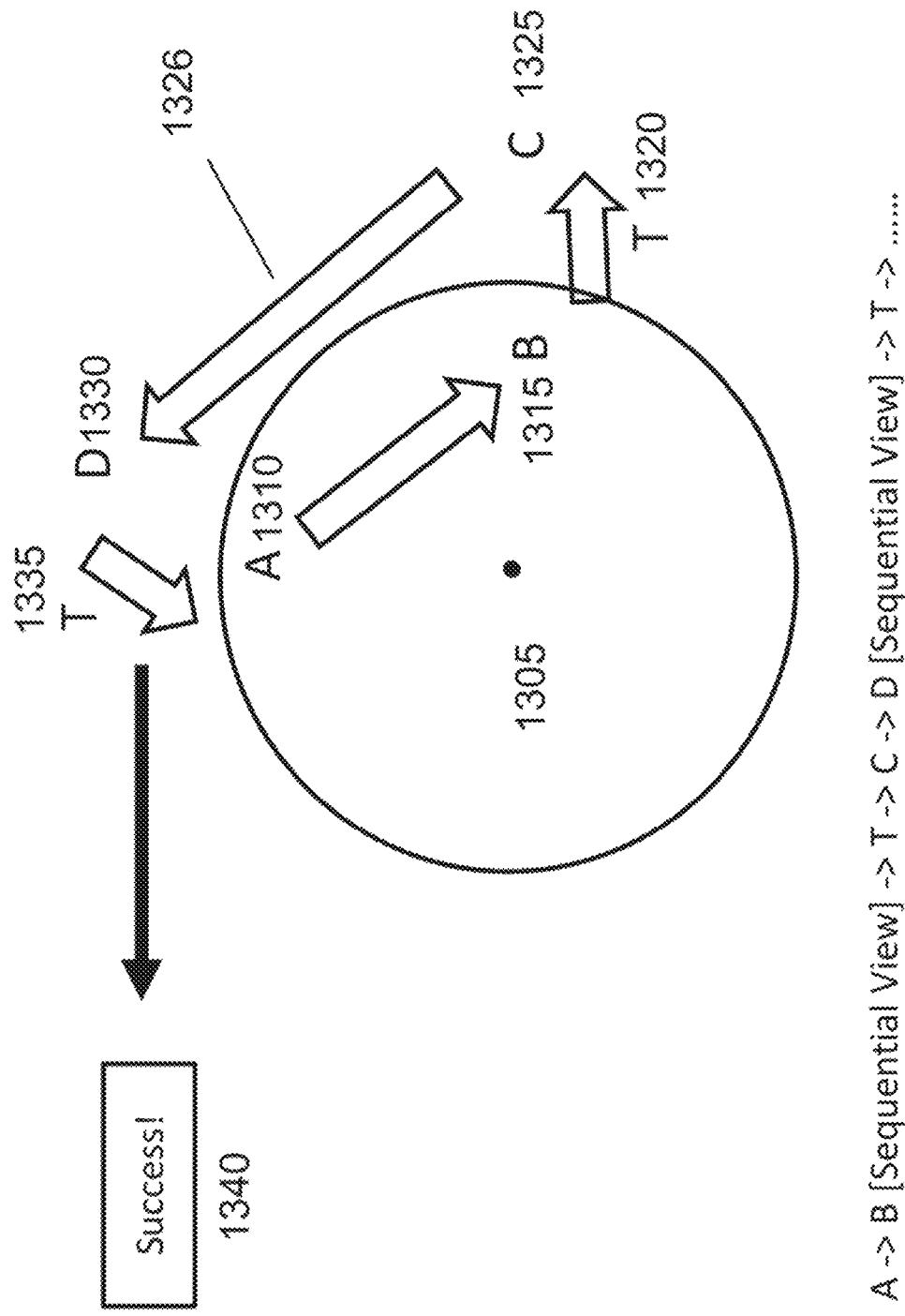
FIG. 13 schematically illustrates shield assembly motion control using sequential view in accordance with some embodiments.

FIG. 13 schematically illustrates movement of the mechanical subsystem to obtain kV images of the identified target in accordance with the sequential viewing methodology. In this concept view of axial rotation from entry, the axial rotation path 1305 is represented by a circle. Target is in the center of that circle 1305 defined by rotational movement of the axial shield. In step 1310, a first kV image is obtained from position A, where the kV X-ray tubes are located at the top and the kV detector is located at the bottom. In step 1315, the axial shield is rotated to position B, where kV X-ray tubes are located at the right and the kV detector is located on the left. In step 1320, the sequential view algorithm uses kV images acquired from position A and B to calculate target offset. Patient table is then moved to compensate for the offset. In step 1325, another kV image is obtained at position C (same as position B except the patient table has been moved). In step 1326, the axial shield is rotated back to position D (same as position A except table has been moved). In step 1330, another kV image is obtained at position D. In step 1335, the sequential view algorithm uses kV images acquired from position C and D to calculate the target offset. The patient table is moved to compensate the offset. In step 1340, if the last calculated offset from step 1335 is less than a pre-defined threshold (for example, 0.5 mm), the initial alignment is finished since the target is aligned at the isocenter; otherwise, the tracking method can repeat steps from step 1310 until the target is aligned.

Figure 14:
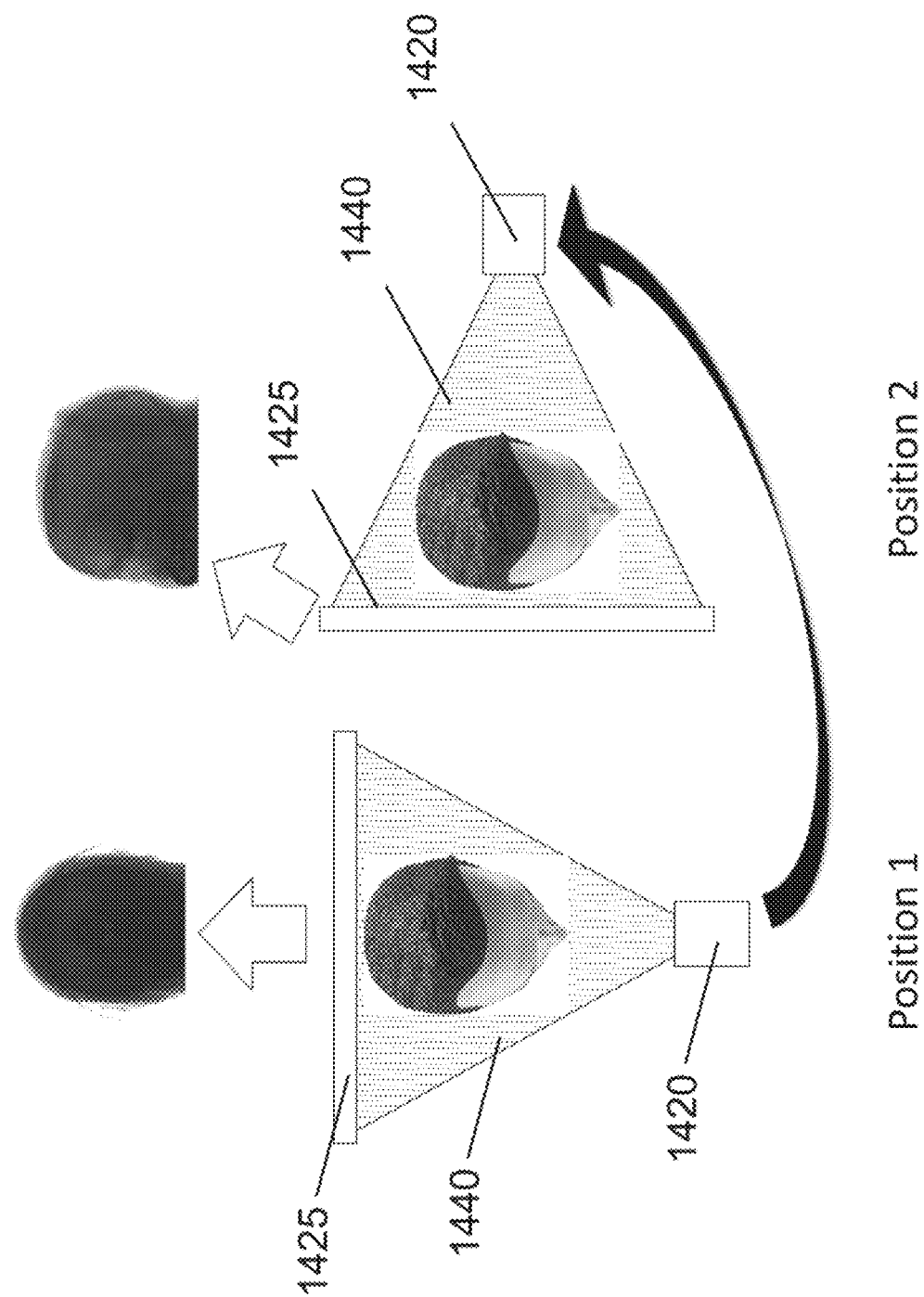
FIG. 14 schematically illustrates first and second positions in sequential view imaging in accordance with some embodiments.

FIG. 14 schematically illustrates imaging at first and second positions in sequential view imaging in accordance with some embodiments. In Position 1, the diagnostic radiation beam emitter 1420 directs a diagnostic imaging beam 1440 through the target, while a diagnostic beam detector unit 1425 measured the residual beam passed through the target. In Position 2, the diagnostic radiation beam emitter 1420 and the detector unit 1425 have been revolved around an axis extending through the isocenter to Position 2, at which a second image is obtained. Typically, the second position is at least 20 degrees from the first position. The first and second images can be utilized, as described previously, to determine a diagnostic result to faciliate delivery of therapy.

While the exemplary embodiments have been described in some detail, by way of example and for clarity of understanding, those of skill in the art will recognize that a variety of modifications, adaptations, and changes may be employed. Hence, the scope of the present invention should be limited solely by the appending claims.

In the foregoing specification, the invention is described with reference to specific embodiments thereof, but those skilled in the art will recognize that the invention is not limited thereto. Various features, embodiments and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. An imaging system to facilitate radiotherapy delivery during a radiotherapy procedure comprising:
   an imaging radiation beam emitter mounted in the system to be in line with an isocenter at which a target is disposed, wherein the imaging radiation beam emitter is configured to revolve about a first axis intersecting the isocenter;
   an imaging radiation beam detector unit mounted in the treatment system opposite the imaging radiation beam emitter, wherein the detector unit is movable independently from the beam emitter; and
   a control unit operably coupled with the imaging radiation beam emitter and detector, the control unit being configured to:
      obtain a first image with the imaging radiation beam emitter and detector at a first position of the emitter; and
      obtain a second image with the imaging radiation beam emitter and detector at second position of the emitter.

2. The imaging system of claim 1, wherein the control unit is further configured to obtain additional images from multiple directions with the imaging radiation beam emitter by rotating the beam emitter about the first axis.

3. The imaging system of claim 1, wherein the imaging system has a single imaging radiation source.

4. The imaging system of claim 3 wherein the single imaging radiation source is a kV radiation tube with an X-ray supply.

5. The imaging system of claim 3, wherein the imaging system has a single imaging radiation detector.

6. The imaging system of claim 5, wherein the radiation beam detector is an amorphous silicon flat panel detector.

7. The imaging system of claim 1, wherein the first and second images are 2D images and the imaging system is further configured to align the target with a 3D image result for radiotherapy delivery according to a treatment plan by usingthe first and second images.

8. The imaging system of claim 7, wherein the first and second positions are at least 20 degrees apart.

9. The imaging system of claim 7, wherein the control unit is further configured to generate a 3D image for radiotherapy delivery according to the treatment plan by comparing and combining the first and second images with a predetermined image associated with the treatment plan.

10. The imaging system of claim 7, wherein the control unit is further configured to generate a 3D image for radiotherapy delivery according to the treatment plan by correlating the first and second images to a digitally reconstructed radiograph (DRR).

11. The imaging system of claim 10, wherein the control unit is further configured to generate the 3D image by combining the first and second images after correlating each to the digitally reconstructed radiograph (DRR).

12. The imaging system of claim 7, wherein the control unit is further configured to determine a displacement matrix between the first and second positions and combine with 2D translation results from the first and second images to generate a depth result.

13. The imaging system of claim 12, wherein the control unit is further configured to combine the depth result with a current location to form a 3D translation result.

14. The imaging system of claim 7, wherein the control unit is further configured to:
  correlate the first image with the DRR image to generate a 2D translation;
  correlate the second image with the DRR image to generate a second 2D translation; and
  generate a 3D translation result based on the 2D translations and compare with the second image for use in controlling delivery of the radiation therapy beam to the target.

15. The imaging system of claim 7, wherein the imaging radiation emitter is mounted in a first shield component of the system that is rotatable about the first axis, and the imaging beam detector is mounted within a second shield component that is rotatable about the second axis.

16. The imaging system of claim 15, wherein the first and second axes are transverse.

17. The imaging system of claim 15, wherein the imaging system is a subsystem within a treatment system having a radiation source configured to deliver a therapeutic beam to the target and mounted within the second shield component to be in line with the isocenter.

18. The imaging system of claim 17, further comprising:
  a control system configured to rotate the second shield component and control delivery of radiotherapy with the therapeutic beam according to the treatment plan based on a current location of the target as determined by the imaging system.

19. The imaging system of claim 1, wherein the controller is configured to:
  determine a first offset of the target from the isocenter based on the first and second images;
  adjust a position of the patient based on the first offset;
  obtain a third image with the imaging beam emitter at a third position, the third position corresponding to the second position adjusted for the first offset;
  obtain a fourth image with the imaging beam emitter at a fourth position, the fourth position corresponding to the first position adjusted for the first offset;
  determine a second offset based on the third and fourth images; and
  adjust a position of the patient based on the second offset.

20. The imaging system of claim 19, wherein the controller is further configured to:
  repeat obtaining additional set of at least two images from at least two positions adjusted for prior determined offsets until a newly determined offset is less than a predefined threshold, thereby indicating the target is aligned with the isocenter.

21. An imaging system to facilitate radiotherapy delivery during a radiotherapy procedure comprising:
  an imaging radiation beam emitter mounted in the system to be in line with an isocenter of the system at which a target is disposed, wherein the imaging radiation beam emitter configured to revolve about a first axis intersecting the isocenter;
  an imaging radiation beam detector unit mounted in the treatment system opposite the imaging radiation beam emitter, wherein the detector unit is movable independently from the beam emitter; and
  a control unit operably coupled with the imaging radiation beam emitter and detector, the control unit being configured to:
    obtain a first image with the imaging radiation beam emitter and detector at a first position of the emitter; and
    generate an imaging result for radiotherapy delivery according to a treatment plan by comparing and combining the first image with a previously generated image of the target.

22. The imaging system of claim 21, wherein the previously generated image is a digital reconstructed radiograph (DRR) image.

23. A method of imaging to facilitate radiotherapy delivery during a radiotherapy procedure comprising:
  obtaining a first image with an imaging radiation beam emitter and an imaging radiation beam detector unit, while the emitter is at a first position, the radiation beam emitter being mounted within an imaging system to be in line with an isocenter of the system at which a target is disposed and the imaging radiation beam emitter mounted in the treatment system opposite the imaging radiation beam emitter, wherein the detector unit is movable independently from the beam emitter;
  obtaining a second image with the imaging radiation beam emitter and detector, when the beam emitter is disposed at second position of the emitter;
  generating an image result for radiotherapy delivery according to a treatment plan using the first and second images.

24. The method of claim 23, wherein the first and second images are 2D images and the control unit is further configured to generate a 3D image result for radiotherapy delivery using the first and second images.

25. The method of claim 24, wherein the first and second positions are at least 20 degrees apart.

26. The method of claim 24, wherein the control unit is further configured to generate the 3D image for radiotherapy delivery by comparing and combining the first and second images.

27. The method of claim 24, wherein the control unit is further configured to generate the 3D image by correlating the first and second images to a digitally reconstructed radiograph (DRR).

28. The method of claim 27, wherein the control unit is further configured to generate the 3D image by combining the first and second images after correlating each to a digitally reconstructed radiograph (DRR).

29. The method of claim 24, further comprising:
  determining a displacement matrix between the first and second positions and combining with 2D translation results from the first and second images to generate a depth result.

30. The method of claim 29, wherein the control unit is further configured to combine the depth result with a current location to form a 3D translation result.

31. The method of claim 24 further comprising:
  determining a first offset of the target from the isocenter based on the first and second images;
  adjusting a position of the patient based on the first offset;
  obtaining a third image with the imaging beam emitter at a third position, the third position corresponding to the second position adjusted for the first offset;

obtaining a fourth image with imaging beam emitter at a fourth position, the fourth position corresponding to the first position adjusted for the first offset;

determining a second offset based on the third and fourth images; and adjusting a position of the patient based on the second offset.

32. The method of claim 31, further comprising:

repeating obtaining additional sets of at least two images from at least two positions adjusted for prior determined offsets until a newly determined offset is less than a predefined threshold, thereby indicating the target is aligned with the isocenter.

33. The method of claim 23 wherein the imaging beam emitter is mounted within a first shield portion and the beam detector is mounted within a second shield portion, wherein moving the imaging beam emitter between the first and second positions comprises rotating the first shield portion about the first axis, with a control unit of the system.

34. The method of claim 33, wherein the imaging system is a subsystem within a treatment system having a radiation source configured to direct a therapeutic beam emitter at the target, the radiation source being mounted within the second shield portion.

35. The method of claim 23, wherein the imaging system has a single imaging radiation source.

36. The method of claim 35, wherein the single imaging radiation source is a kV radiation tube with an X-ray supply.

37. The method of claim 35 wherein the imaging system has a single imaging radiation detector.

38. The method of claim 37 wherein the radiation beam detector is an amorphous silicon flat panel detector.

39. A method of imaging to facilitate radiotherapy delivery during a radiotherapy procedure comprising:

obtaining a first image with an imaging radiation beam emitter and an imaging radiation beam detector unit, when the emitter is at a first position, the radiation beam emitter being mounted within an imaging system to be in line with an isocenter of the system at which a target is disposed and the imaging radiation beam emitter mounted in the treatment system opposite the imaging radiation beam emitter, wherein the detector unit is movable independently from the beam emitter;

comparing the first image with a previously generated image of the target; and generating an imaging result from the comparison for delivery of radiotherapy.

40. The method of claim 39, wherein the previously generated image is a digitally reconstructed radiograph (DRR).

* * * * *

UNITED STATES PATENT AND TRADEMARK OFFICE
CERTIFICATE OF CORRECTION

PATENT NO. : 12,220,270 B2
APPLICATION NO. : 17/398798
DATED : February 11, 2025
INVENTOR(S) : Younes Achkire et al.

Page 1 of 1

It is certified that error appears in the above-identified patent and that said Letters Patent is hereby corrected as shown below:

In the Claims

In Column 22 Line 35: "detector at second position" should read -- detector at a second position --.

In Column 22 Line 53: "usingthe first and" should read -- using the first and --.

In Column 23 Line 11: "The imaging system of claim 7, wherein" should read -- The imaging system of claim 10, wherein --.

In Column 23 Lines 65-66: "radiation beam emitter configured" should read -- radiation beam emitter is configured --.

Signed and Sealed this
Eighteenth Day of November, 2025

John A. Squires
*Director of the United States Patent and Trademark Office*